(12) United States Patent
Shen et al.

(10) Patent No.: US 7,078,382 B1
(45) Date of Patent: Jul. 18, 2006

(54) MODULATION OF ENOS ACTIVITY AND THERAPEUTIC USES THEREOF

(75) Inventors: Ben-Quan Shen, San Francisco, CA (US); Thomas Zioncheck, Montara, CA (US)

(73) Assignee: Genentech, Inc., South San Francisco, CA (US)

( * ) Notice: Subject to any disclaimer, the term of this patent is extended or adjusted under 35 U.S.C. 154(b) by 408 days.

(21) Appl. No.: 09/700,806

(22) PCT Filed: Nov. 2, 2000

(86) PCT No.: PCT/US00/30294

§ 371 (c)(1),
(2), (4) Date: Mar. 12, 2002

(87) PCT Pub. No.: WO01/32695

PCT Pub. Date: May 10, 2001

Related U.S. Application Data

(60) Provisional application No. 60/163,132, filed on Nov. 2, 1999.

(51) Int. Cl.
*A61K 38/18* (2006.01)
*C07K 14/475* (2006.01)

(52) U.S. Cl. .................... 514/12; 530/350; 530/399
(58) Field of Classification Search ............ 514/2; 530/399; 536/23.1
See application file for complete search history.

(56) References Cited

U.S. PATENT DOCUMENTS

| | | | |
|---|---|---|---|
| 3,773,919 A | 11/1973 | Boswell | |
| 3,887,699 A | 6/1975 | Yolles | |
| 4,816,567 A | 3/1989 | Cabilly et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,851,999 A * | 12/1998 | Ullrich et al. | 514/44 |
| 5,955,311 A | 9/1999 | Rockwell et al. | |
| 6,020,473 A * | 2/2000 | Keyt et al. | 536/23.1 |
| 6,057,428 A * | 5/2000 | Keyt et al. | 530/399 |
| 6,239,172 B1 * | 5/2001 | Kaesemeyer | 514/460 |
| 6,352,975 B1 | 3/2002 | Schreiner et al. | |
| 6,395,707 B1 * | 5/2002 | Zioncheck et al. | 514/12 |
| 6,475,796 B1 * | 11/2002 | Pollitt et al. | 435/455 |
| 6,485,942 B1 * | 11/2002 | Zioncheck et al. | 435/69.4 |

FOREIGN PATENT DOCUMENTS

| | | |
|---|---|---|
| CA | 1176565 | 10/1984 |
| EP | 36776 | 9/1981 |
| EP | 058481 | 8/1982 |
| EP | 75444 | 3/1983 |
| EP | 158277 | 10/1985 |
| GB | WO 98/20027 * | 5/1998 |
| WO | WO 90/13649 | 11/1990 |
| WO | WO 97/08313 | 3/1997 |
| WO | WO 98/16551 | 4/1998 |
| WO | WO 98/20027 | 5/1998 |
| WO | WO 00/13702 | 3/2000 |
| WO | WO 00/63380 | 10/2000 |
| WO | WO 00/71713 | 11/2000 |

OTHER PUBLICATIONS

Pagliaro (2003), Life Sci 73(17): 2137-2149.*
Marin et al. (1997), Pharmacol Ther 75(2): 111-134.*
Gerber et al. (1998), J. Biol. Chem. 273(46): 30336-30343.*
El-Mahmoudy et al. (2005), Int. Immunopharm. 5: 195-207.*
Kroll et al. (1998), Biochem. Biophys. Res. Comm. 252: 743-746.*
Van Belle et al. (1997), Biochem. Biophys. Res. Comm. 235: 311-316.*
Losordo et al. (1998), Circulation, 98: 2800-2804.*
Rosengart et al. (1999), Circulation 100: 468-474.*
Isner et al. (1999), Nat. Med. 5(5): 491-492.*
Bolivar et al., Gene, 2:95-113 (1977) Construction and Characterization of New Cloning Vehicles.
Cohen, Proc. Natl. Acad. Sci., (USA), 69:8, 2110-2114 (1972) Nonchromosomal Antibiotic Resistance in Bacteria: Genetic Transformation of *Escherichia coli* by R-Factor DNA.
Fiers et al., Nature, 273:113-120 (1978) Complete Nucleotide Sequence of SV40 DNA.

(Continued)

*Primary Examiner*—Marianne P. Allen
(74) *Attorney, Agent, or Firm*—Merchant & Gould P.C.

(57) ABSTRACT

The present invention provides uses of VEGF or VEGF receptor agonists for the up-regulation of eNOS expression and activity. VEGF and VEGF receptor agonists are useful in the treatment of or prevention from hypertension, diabetes, angina, thrombosis, atherosclerosis, heart failure, and other conditions or disorders wherein nitric oxide is an important regulator.

12 Claims, 20 Drawing Sheets

OTHER PUBLICATIONS

Goeddel et al., Nature, 281:544-548 (1979) Direct Expression in *Escherichia coli* of a NDA Sequence Coding for Human Growth Hormone.

Goeddel et al., Nucleic Acids Res., 8:18, pp. 4057-4074 (1980) Synthesis of Human Fibroblast Interferon by *E coli*.

Graham and van der Eb, Virology, 52:456-467 (1978) A New Technique for the Assay of Infectivity of Human Adenovirus 5 DNA.

Hitzeman et al., J. Biol. Chem., 255:24, pp. 2073-12080 (1980) Isolation and Characterization of the Yeast 3-Phosphoglycerokinase Gene (PGK) by an Immunological Screening Technique.

Hess et al., J. Adv. Enzyme Reg., 7:149-167 (1968) Cooperation of Glycolytic Enzymes.

Holland et al., Biochemistry, 17:23, pp. 4900-4907 (1978) Isolation and Identification of Yeast Messenger Ribonucleic Acids Coding for Enolase, Glyceralydehyde-3-phosphate Dehydrogenase, and Phosphoglycerate Kinase.

Hsiao et al., Proc. Natl. Acad. Sci. (USA), 76:8, pp. 3829-3833 (1979) High-frequency Transformation of Yeast by Plasmids Containing the Clined Yeat ARG$^4$ Gene.

Ishikawa et al., Nature, 338:557 (1989) Identification of Angiogenic Activity and the Cloning and Expression of Platelet-derived Endotheilial Cell Growth Factor.

Itakura et al., Science, 198:1056-1063 (1977) Expression is *Escherichia coli* of a Chemically Synthesized Gene for the Hormone Somatostatin.

Jones, Genetics, 85:23-33 (1977) Proteinase Mutants of *Saccharomyces cerevisiae*.

Keyt et al., J. Biol. Chem., 271:10, pp. 5638-5646 (1996) Identification of Vascular Endothelial Growth Factor Determinants for Binding KDR and FLT-1 Receptors.

Kingsman et al., Gene 7:141-152 (1979) Replication in *Saccharomyces cerevisiase* of Plasmid pBR313 Carrying DNA from the Yeast trpl Region.

Kunkel et al., Meth. Enzym. 204:125-139 (1991) Efficient Site-Directed Mutagenesis Using Uracil-Containing DNA.

Laboratory Investigation, 72:615 (1995) Vascular Endothelial Growth Factor.

Oates, Chapter 33, Goodman and Gilman, 9th Edition, pp. 780-781. Antihypertensive Agents and the Drug Therapy of Hypertension.

Mandel et al., J. Mol. Biol., 53:159-162 (1970) Calcium-dependent Bacteriophase DNA Infection.

Maxam et al., Methods of Enzymology, 65:499 (1977) Sequencing End-Labeled DNA with Base-Specific Chemical Cleavages.

Messing et al., Nucleic Acids res., 9:2, pp. 309-321 (1981) A System for Shotgun DNA Sequencing.

Siebenlist et al., Cell, 20:269-281 (1980) *E. coli* RNA Polymerase Interacts Homologously with Two Different Promoters.

Stinchcomb et al., Nature, 282:39-43 (1979) Isolation and Characterisationof a Yeast Chromosomal Replicator.

Tschumper et al., Gene, 10:157-166 (1980) Sequence of a Yeast DNA Fragment Containing a Chromosomal Replicator and the TRP1 Gene.

Urlaub and Chasin, Proc. Natl. Acad. Sci. (USA), 77:4, pp. 4216-4220 (1980) Isolation of Chinese Hamster Cell Mutants Deficient in Dihydrofolate Reductase Activity.

VAn Solingen et al., J. Bact., 130:946-947 (1977) Fusion of Yeast Spheroplasts.

Boerner et al., "Production of Antigen-Specific Human Monoclonal Antibodies From In Vitro-Primed Human Splenocytes" *The Journal of Immunology* 147(1):86-95 (1991).

Burgess and Maciag, "The Heparin-Binding (Fibroblast) Growth Factor Family of Proteins" *Annu. Rev. Biochem.* 58:575-606 (1989).

Busse and Fleming., "Endothelial Dysfunction in Atherosclerosis." *J. Vasc. Res.* 33:181-194 (1996).

Cao, Yihai et al., "Heterodimers of Placenta Growth Factor/Vascular Endothelial Growth Factor." *J. Bio. Chem.* 271:3154-3162 (1996).

De Vries et al., "The fms-Like Tyrosine Kinase, A Receptor for Vascular Endothelial Growth Factor." *Science.* 255:989-991 (Feb. 1992).

Drumond and Harrison., "eNOS-Overexpressing Mice: Too Much NO Makes the Blood Pressure Low." *J. Clin. Invest.* 102:2033-2034 (Dec. 1998).

Ferrara and Davis-Smyth., "The Biology of Vascular Endothelial Growth Factor." *Endocrine Reviews.* 18(1):4-25 (1997).

Ferrara and Henzel, "Pituitary Follicular Cells Secrete a Novel Heparin-binding Growth Factor Specific for Vascular Endothelial Cells" *Biochem. & Biophys. Res. Comm.* 161(2):851-858 (1989).

Fishwild et al., "High-Avidity Human IgGκ Monoclonal Antibodies From a Novel Strain of Minilocus Transgenic Mice" *Nature Biotechnology.* 14(7):845-851 (Jul. 1996).

Folkman., "Angiogenesis in Cancer, Vascular, Rheumatoid and Other Disease." *Nature Medicine.* 1(1):27-31 (1995).

Fuh et al., "Reguirements for Binding and Signaling of the Kinase Domain Receptor for Vascular Endothelial Growth Factor." *J. Bio. Chem.* 273(18):11197-11204 (May 1, 1998).

Hariawala et al., "VEGF Improves Myocardial Blood Flow but Produces EDRF-Mediated Hypotension in Porcine Hearts." *J. Surg. Res.* 63:77-82 (1996).

Hood et al., "VEGF Upregulates ecNOS Message, Protein, and NO Production in Human Endothelial Cells." *Am. J. Phys.* 274:H1054-H1058 (1998).

Hoogenboom and Winter, "By-Passing Immunisation: Human Antibodies from Synthetic Repertoires of Germline $V_H$ Gene Segments Rearranged in Vitro" *J. Mol. Biol.* 227:381-388 (1992).

Houck et al., "The Vascular Endothelial Growth Factor Family: Identification of a Fourth Molecular Species and Characterization of Alternative Splicing of RNA." *Mol. Endocrinol.* 5:1806-1814 (1991).

Ishikawa et al., "Identification of Angiogenic Activity and the Cloning and Expression of Platelet-Derived Endothelial Cell Growth Factor." *Nature.* 338:557-562 (1989).

Jin et al., "Novel Analog of Atrial Natriuretic Peptide Selective for Receptor-A Produces Increased Diuresis and Natriuresis in Rats." *J. Clinical Investigation.* 98(4):969-976 (Aug. 15, 1996).

Jones et al., "Replacing the Complementarity-Determining Regions in a Human Antibody with those from a Mouse" *Nature* 321:522-525 (May 29, 1986).

Keyt et al., "Identification of Vascular Endothelial Growth Factor Determinants for Binding KDR and FLT-1 Receptors: Generation of Receptor-Selective VEGF Variants by Site-Directed Mutagenesis." *Journal of Biological Chemistry* 271(10):5638-5646 (1996).

Keyt et al., "The Carboxyl-terminal Domain (111-165) of Vascular Endothelial Growth Factor Is Critical for Its Mitogenic Potency" *Journal of Biological Chemistry* 271(13):7788-7795 (Mar. 29, 1996).

Kroll et al., "VEGF-A Induces Expression of eNOS and iNOS in Endothelial Cells via VEGF Receptor-2 (KDR)." *Biochem. & Biophys. Res. Comm.* 252:743-746 (1998).

Langer., "Controlled Release of Macromolecules." *Chemtech.* 12:98-105 (Feb. 1982).

Leung et al., "Vascular Endothelial Growth Factor is a Secreted Angiogenic Mitogen" *Science* 246:1306-1309 (1989).

Liu et al., "Angiogenesis Activators and Inhibitors Differentially Regulate Caveolin-1 Expression and Caveolae Formation in Vascular Endothelial Cells." *J. Bio. Chem.* 274:15781-15785 (1999).

Lonberg and Huszar., "Human Antibodies From Transgenic Mice" *International Reviews of Immunology* 13(1):65-93 (1995).

Lonberg et al., "Antigen-Specific Human Antibodies From Mice Comprising Four Distinct Genetic Modifications" *Nature.* 368(6474):856-859 (Apr. 28, 1994).

Luscher., "Endogenous and Exogenous Nitrates and Their Role in Myocardial Ischaemia." *Br. J. Clin. Pharmacol.* (Suppl. 1) 34:29S-35S (1992).

Malavaud et al., "Activation of Flk-1/KDR Mediates Angiogenesis but not Hypotension." *Cardiovascular Research.* 36(2):276-281 (Nov. 1997).

Marks et al., "By-Passing Immunization: Building High Affinity Human Antibodies by Chain Shuffling" *Bio/Technology* 10:779-783 (1992).

Marks et al., "By-Passing Immunization: Human Antibodies From V-gene Libraries Displayed on Phage" *J. Mol. Biol.* 222:581-597 (1991).

Matthews et al., "A Receptor Tyrosine Kinase cDNA Isolated from a Population of Enriched primitive Hematopoietic Cells and Exhibiting Close Genetic Linkage to c-kit." *Proc. Natl. Acad. Sci.* 88:9026-9030 (1991).

Meyer et al., "A Novel Vascular Endothelial Growth Factor Encoded by Orf Virus, VEGF-E, Mediates Angiogenesis Via Signalling Through VEGFR-2 (KDR) but not VEGFR-1 (Flt-1) Receptor Tyrosine Kinases." *EMBO Journal* 18(2):363-374 (Jan. 15, 1999).

Migdal et al., "Neuropilin-1 is a Placenta Growth Factor-2 Receptor." *J. Bio. Chem.* 273:22272-22278 (Aug. 1998).

Morbidelli et al., "Nitric Oxide Mediates Mitogenic Effect of VEGF on Coronary Venular Endothelium." *Am. J. Physiol.* 270:H411-H415 (1996).

Morrison et al., "Chimeric Human Antibody Molecules: Mouse Antigen-Binding Domains with Human Constant Region Domains" *Proc. Natl. Acad. Sci. USA* 81:6851-6855 (Nov. 1984).

Morrison, S., "Immunology: Success in Specification" *Nature.* 368(6474):812-813 (Apr. 28, 1994).

Muller et al., "The Crystal Structure of Vascular Endothelial Growth Factor (VEGF) Refined to 1.93 A Resolution: Multiple Copy Flexibility and Receptor Binding." *Structure.* 5(10):1325-1338 (Oct. 15, 1997).

Muller et al., "Vascular Endothelial Growth Factor: Crystal Structure and Functional Mapping of the Kinase Domain Receptor Binding Site." *Proc. Natl. Acad. Sci. USA* 94(14):7192-7197 (Jul. 8, 1997).

Murohara et al., "Nitric Oxide Synthase Modulates Angiogensis in Reponse to Tissue Ischemia." *J. Clin. Invest.* 101:2567-2578 (Jun. 1998).

Nathan and Xie, "Regulation of Biosynthesis of Nitric Oxide." *J. Bio. Chem.* 269:13725-13728 (May 1994).

Neuberger, M., "Generating High-Avidity Human Mabs in Mice" *Nature Biotechnology.* 14(7):826 (Jul. 1996).

Ogawa et al., "A Novel Type of Vascular Endothelial Growth Factor, VEGF-E (NZ-7 VEGF), Preferentially Utilizes KDR/Flk-1 Receptor and Carries a Potent Mitotic Activity Without Heparin-Binding Domain." *J. Bio. Chem.* 273(47):31273-31282 (Nov. 20, 1998).

Ohashi et al,. "Hypotension and Reduced Nitric Oxide-Elicited Vasorelaxation in Transgenic Mice Overexpressing Endothelial Nitric Oxide Synthase." *J. Clin. Invest.* 102:2061-2071 (Dec. 1998).

Olofsson et al., "Vascular Endothelial Growth Factor B (VEGF-B) Binds to VEGF Receptor-1 and Regulates Plasminogen Activator Activity in Endothelial Cells." *Proc. Natl. Acad. Sci. USA* 95(20):11709-11714 (Sep. 29, 1998).

Papapetropoulos et al., "Nitric Oxide Production Contributes to the Angiogenic Properties of Vascular Endothelial Growth Factor in Human Endothelial Cells." *J. Clin Invest.* 100:3131-3139 (Dec. 1997).

Parenti et al., "Nitric Oxide is an Upstream Signal of Vascular Endothelial Growth Factor-Induced Extracellular Signal-Regulated Kinase$_{1/2}$ Activation in Postcapillary Endothelium." *J. Bio. Chem.* 273:4220-4226 (Feb. 1998).

Pepper., "Manipulating Angiogenesis: From Basic Science to the Bedside." *Arterioscler. Thromb. Vasc. Bio.* 17:605-619 (1997).

Presta, L., "Antibody Engineering" *Curr. Op. Struct. Biol.* 2:593-596 (1992).

Riechmann et al., "Reshaping Human Antibodies for Therapy" *Nature* 332:323-327 (Mar. 24, 1988).

Rudic et al., "Direct Evidence for the Importance of Endothelium-Derived Nitric Oxide in Vascular Remodeling." *J. Clin. Invest.* 101:731-736 (Feb. 1998).

Sase and Michel., "Expression and Regulation of Endothelial Nitric Oxide Synthase." *Trends Cardiovasc. Med.* 7:28-37 (1997).

Shen et al., "Hepatocyte Growth Factor Stimulates the Differentiation of the Human Tracheal Epithelia In Vitro." *Am. J. Physiol.* 272:L1115-L1120 (1997).

Shen et al., "Homologous Up-Regulation of the KDR/Flk-1 Receptor Expression by Vascular Endothelial Growth Factor In Vitro." *J. Bio. Chem.* 273:29979-29985 (Nov. 1998).

Shibuya et al., "Nucleotide Sequence and Expression of a Novel Human Receptor-Type Tyrosine Kinase Gene (flt) Closely Related to the fms Family." *Oncogene* 5:519-524 (1990).

Sidman et al., "Controlled Release of Macromolecules and Pharmaceuticals from Synthetic Polypeptides Based on Glutamic Acid" *Biopolymers* 22(1):547-556 (1983).

Siemeister et al., "Expression of Biologically Active Isoforms of the Tumor Angiogenesis Factor VEGF in *Escherichia coli.*" *Biochem. & Biophys. Res. Comm.* 222:249-255 (1996).

Soker et al., "Neuropilin-1 is Expressed by Endothelial and Tumor Cells as an Isoform-Specific Receptor for Vascular Endothelial Growth Factor." *Cell.* 92:735-745 (Mar. 1998).

Terman et al., "Identification of a New Endothelial Cell Growth Factor Receptor Tyrosine Kinase." *Oncogene.* 6:1677-1683 (1991).

Terman et al., "Identification of the KDR Tyrosine Kinase as a Receptor for Vascular Endothelial Cell Growth Factor." *Biochem. & Biophys. Res. Comm.* 187:1579-1586 (1992).

Tischer et al., "Vascular Endothelial Growth Factor: A New Member of the Platelet-Derived Growth Factor Gene Family." *Biochem. & Biophys. Res. Comm.* 165:1198-1206 (1989).

van der Zee et al., "Vascular Endothelial Growth Factor/Vascular Permeability Factor Augments Nitric Oxide Release From Quiescent Rabbit and Human Vascular Endothelium." *Circulation.* 95:1030-1037 (1997).

Verhoeyen, M. et al., "Reshaping Human Antibodies: Grafting an Antilysozyme Activity" *Science* 239:1534-1536 (Mar. 25, 1988).

Waltenberger et al., "Different Signal Transduction Properties of KDR and Flt1, Two Receptors for Vascular Endothelial Growth Factor." *J. Bio. Chem.* 269(43):26988-26995 (Oct. 28, 1994).

Weismann et al., "Crystal Structure at 1.7 A Resolution of VEGF in Complex with Domain 2 of the Flt-1 Receptor." *Cell.* 91:695-704 (Nov. 1997).

Wu et al., "VEGF Induces NO-Dependent Hyperpermeability in Coronary Venules." *Am. J. Physiol.* 271:H2735-H2739 (1996).

Yang et al., "Effects of Vascular Endothelial Growth Factor on Hemodynamics and Cardiac Performance." *J. Cardiovasc. Pharmacol.* 27:838-844 (1996).

Ziche et al., "Nitric Oxide Synthase Lies Downstream from Vascular Endothelial Growth Factor-Induced but not Basic Fibroblast Growth Factor-Induced Angiogensis." *J. Clin. Invest.* 99:2625-2634 (Jun. 1997).

Harada, K. et al., "Vascular endothelial growth factor administration in chronic myocardial ischemia," *The American Physiological Society*, pp. H1791-H1802(© 1996).

Laitinen, M. et al., "VEGF Gene Transfer Reduces Intimal Thickening via Increased Production of Nitric Oxide in Carotid Arteries," *Human GeneTherapy*, vol. 8, No. 15, pp. 1737-1744 (Oct. 10, 1997).

Morbidelli, L. et al., "Nitric oxide mediates mitogenic effect of VEGF on coronary venular endothelium," *The American Pyhsiological Society*, pp. H411-H415 (© 1996).

Zachary, L. et al., "Vascular endothelial growth factor stimulates nitric oxide production and prostacyclin synthesis in human umbilical endothelial cells," *Journal of the European Society of Cardiology*, Abstract Supplement, vol. 18 ISSN 0195 668X, 3 pages (Aug. 1997).

Bouloumié et al., 1999, *Cardiovascular Research*, 41:773-780 "Vascular endothelial growth factor up-regulates nitric oxide synthase expression in endothelial cells."

Kroll et al., 1999, *Biochemical and Biophysical Research Communications*, 265:636-639 "A Novel Function of VEGF Receptor-2 (KDR); Rapid Release of Nitric Oxide in Response to VEGF-A Stimulation in Endothelial Cells."

* cited by examiner

| | |
|---|---|
| △ | vehicle control |
| ▲ | VEGF |
| □ | L-NAME |
| ■ | VEGF+ L-NAME |
| ○ | SNAP |
| ● | VEGF+ SNAP |

SEQUENCE LISTING

<160> NUMBER OF SEQ ID NOS: 4

<210> SEQ ID NO 1
<211> LENGTH: 57
<212> TYPE: DNA
<213> ORGANISM: Artificial Sequence
<220> FEATURE:
<221> NAME/KEY: Misc_feature
<222> LOCATION: 1-57
<223> OTHER INFORMATION: Sequence is synthesized.
<221> NAME/KEY: unsure
<222> LOCATION: 19, 20, 21, 28, 29, 30, 31, 32, 33, 40, 41, 42
<223> OTHER INFORMATION: N at indicated positions may be G, A, T or C;
      S at indicated positions may be C or G

<400> SEQUENCE: 1
cacgaagtgg tgaagttcnn sgatgtcnns nnscgcagcn nstgccatcc        50
aatcgag                                                       57

<210> SEQ ID NO 2
<211> LENGTH: 42
<212> TYPE: DNA
<213> ORGANISM: Artificial Sequence
<220> FEATURE:
<221> NAME/KEY: Misc_feature
<222> LOCATION: 1-42
<223> OTHER INFORMATION: Sequence is synthesized.
<221> NAME/KEY: unsure
<222> LOCATION: 16, 17, 18, 22, 23, 24, 25, 26, 27
<223> OTHER INFORMATION: N at indicated positions may be G, A, T or C;
      S at indicated positions may be C or G

<400> SEQUENCE: 2 ggggctgct gcaatnnsga gnnsnnsgag tgtgtgccca ct                 42

<210> SEQ ID NO 3
<211> LENGTH: 990
<212> TYPE: DNA
<213> ORGANISM: Homo sapiens

<400> SEQUENCE: 3
cagtgtgctg gcggcccggc gcgagccggc ccggccccgg tcgggcctcc        50
gaaaccatga actttctgct gtcttgggtg cattggagcc tcgccttgct       100
gctctacctc caccatgcca agtggtccca ggctgcaccc atggcagaag       150
gaggagggca gaatcatcac gaagtggtga agttcatgga tgtctatcag       200
cgcagctact gccatccaat cgagaccctg gtggacatct tccaggagta       250
ccctgatgag atcgagtaca tcttcaagcc atcctgtgtg ccctgatgc        300 gatgcggggg ctgctgcaat gacgagggcc tggagtgtgt gcccactgag       350
gagtccaaca tcaccatgca gattatgcgg atcaaacctc accaaggcca       400
gcacatagga gagatgagct tcctacagca caacaaatgt gaatgcagac       450
caaagaaaga tagagcaaga caagaaaatc cctgtgggcc ttgctcagag       500
cggagaaagc atttgtttgt acaagatccg cagacgtgta aatgttcctg       550
caaaaacaca gactcgcgtt gcaaggcgag gcagcttgag ttaaacgaac       600
gtacttgcag atgtgacaag ccgaggcggt gagccgggca ggaggaagga       650
gcctccctca gggtttcggg aaccagatct ctcaccagga aagactgata       700
cagaacgatc gatacagaaa ccacgctgcc gccaccacac catcaccatc       750

```
gacagaacag tccttaatcc agaaacctga aatgaaggaa gaggagactc        800
tgcgcagagc actttgggtc cggagggcga gactccggcg gaagcattcc        850
cgggcgggtg acccagcacg gtccctcttg gaattggatt cgccatttta        900
tttttcttgc tgctaaatca ccgagcccgg aagattagag agttttattt        950
ctgggattcc tgtagacaca ccgcggccgc cagcacactg                   990
```

<210> SEQ ID NO 4
<211> LENGTH: 191
<212> TYPE: PRT
<213> ORGANISM: Homo sapiens

<400> SEQUENCE: 4

```
Met Asn Phe Leu Leu Ser Trp Val His Trp Ser Leu Ala Leu Leu
 1               5                  10                  15

Leu Tyr Leu His His Ala Lys Trp Ser Gln Ala Ala Pro Met Ala
                20                  25                  30

Glu Gly Gly Gly Gln Asn His His Glu Val Val Lys Phe Met Asp
                35                  40                  45

Val Tyr Gln Arg Ser Tyr Cys His Pro Ile Glu Thr Leu Val Asp
                50                  55                  60

Ile Phe Gln Glu Tyr Pro Asp Glu Ile Glu Tyr Ile Phe Lys Pro
                65                  70                  75

Ser Cys Val Pro Leu Met Arg Cys Gly Gly Cys Cys Asn Asp Glu
                80                  85                  90

Gly Leu Glu Cys Val Pro Thr Glu Glu Ser Asn Ile Thr Met Gln
                95                 100                 105

Ile Met Arg Ile Lys Pro His Gln Gly Gln His Ile Gly Glu Met
               110                 115                 120

Ser Phe Leu Gln His Asn Lys Cys Glu Cys Arg Pro Lys Lys Asp
               125                 130                 135

Arg Ala Arg Gln Glu Asn Pro Cys Gly Pro Cys Ser Glu Arg Arg
               140                 145                 150

Lys His Leu Phe Val Gln Asp Pro Gln Thr Cys Lys Cys Ser Cys
               155                 160                 165

Lys Asn Thr Asp Ser Arg Cys Lys Ala Arg Gln Leu Glu Leu Asn
               170                 175                 180

Glu Arg Thr Cys Arg Cys Asp Lys Pro Arg Arg
               185                 190
```

MODULATION OF ENOS ACTIVITY AND THERAPEUTIC USES THEREOF

This application is a 35 U.S.C. § 371 National Stage filing of PCT/US00/30294, filed on Nov. 2, 2000, which claims the benefit under 35 U.S.C. § 119(e) of U.S. Provisional Application No. 60/163,132, filed on Nov. 2, 1999.

FIELD OF THE INVENTION

The present invention relates to the use of VEGF, and variants thereof, VEGF receptor agonists, and other agents to modulate the endothelial nitric oxide synthase (eNOS) activity. In particular, modulation of eNOS activity is used to treat or prevent mammalian diseases or disorders associated with vascular endothelial cell dysfunction.

BACKGROUND OF THE INVENTION

The two major cellular components of the vasculature are the endothelial and smooth muscle cells. The endothelial cells form the lining of the inner surface of all blood vessels and constitute a nonthrombogenic interface between blood and tissue. In addition, endothelial cells are an important component for the development of new capillaries and blood vessels. Thus, endothelial cells proliferate during the angiogenesis, or neovascularization, associated with tumor growth and metastasis, as well as a variety of non-neoplastic diseases or disorders.

Various naturally occurring polypeptides reportedly induce the proliferation of endothelial cells. Among those polypeptides are the basic and acidic fibroblast growth factors (FGF), Burgess and Maciag, *Annual Rev. Biochem.*, 58:575 (1989), platelet-derived endothelial cell growth factor (PD-ECGF), Ishikawa et al., *Nature*, 338:557 (1989), and vascular endothelial growth factor (VEGF), Leung et al., *Science*, 246:1306 (1989); Ferrara and Henzel, *Biochem. Biophys. Res. Commun.*, 161:851 (1989); Tischer et al., *Biochem. Biophys. Res. Commun.*, 165:1198 (1989); Ferrara et al., PCT Pat. Pub. No. WO 90/13649 (published Nov. 15, 1990).

VEGF has been reported as a key regulator of angiogenesis and vasculogenesis. Ferrara and Davis-Smyth (1997) *Endocrine Rev.* 18:4–25. Compared to other growth factors that contribute to the processes of vascular formation, VEGF is unique in its high specificity for endothelial cells. It is important not only for normal physiological processes such as wound healing, the female reproductive tract, bone/cartilage formation and embryonic formation, but also during the development of conditions or diseases that involve pathological angiogenesis, for example, tumor growth, age-related macular degeneration (AMD) and diabetic retinopathy. Ferrara and Davis-Smyth (1997), supra; Folkman J. (1995) *Nature Med.* 1:27–31; Pepper MS. (1997) *Arterioscler Thromb. Vasc. Biol.* 17:605–619.

In addition to being an angiogenic factor in angiogenesis and vasculogenensis, VEGF, as a pleiotropic growth factor, exhibits multiple biological effects in other physiological and pathological processes, such as endothelial cell survival, vessel permeability and vasodilation, monocyte chemotaxis and calcium influx. Ferrara and Davis-Smyth (1997), supra.

VEGF was first identified in media conditioned by bovine pituitary follicular or folliculostellate cells. Biochemical analyses indicate that bovine VEGF is a dimeric protein with an apparent molecular mass of approximately 45,000 Daltons and with an apparent mitogenic specificity for vascular endothelial cells. DNA encoding bovine VEGF was isolated by screening a cDNA library prepared from such cells, using oligonucleotides based on the amino-terminal amino acid sequence of the protein as hybridization probes.

Human VEGF was obtained by first screening a cDNA library prepared from human cells, using bovine VEGF cDNA as a hybridization probe. One cDNA identified thereby encodes a 165-amino acid protein having greater than 95% homology to bovine VEGF; this 165-amino acid protein is typically referred to as human VEGF (hVEGF) or $VEGF_{165}$. The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. [See Leung et al., *Science*, 246:1306 (1989)].

Although a vascular endothelial cell growth factor could be isolated and purified from natural sources for subsequent therapeutic use, the relatively low concentrations of the protein in follicular cells and the high cost, both in terms of effort and expense, of recovering VEGF proved commercially unavailing. Accordingly, further efforts were undertaken to clone and express VEGF via recombinant DNA techniques. [See, e.g., *Laboratory Investigation*, 72:615 (1995), and the references cited therein].

VEGF is expressed in a variety of tissues as multiple homodimeric forms (121, 145, 165, 189, and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release a diffusible form(s) of VEGF. Amino acid sequencing of the carboxy terminal peptide identified after plasmin cleavage is $Arg_{110}$–$Ala_{111}$. Amino terminal "core" protein, VEGF (1–110) isolated as a homodimer, binds neutralizing monoclonal antibodies (such as the antibodies referred to as 4.6.1 and 3.2E3.1.1) and soluble forms of FLT-1 and KDR receptors with similar affinity compared to the intact $VEGF_{165}$ homodimer.

Certain VEGF-related molecules have also been identified. Ogawa et al. described a gene encoding a polypeptide (called VEGF-E) with about 25% amino acid identity to mammalian VEGF. The VEGF-E was identified in the genome of Orf virus (NZ-7 strain), a parapoxvirus that affects sheep and goats and occasionally, humans, to generate lesions with angiogenesis. The investigators conducted a cell proliferation assay and reported that VEGF-E stimulated the growth of human umbilical vein endothelial cells as well as rat liver sinusoidal endothelial cells to almost the same degree as human VEGF. Binding studies were also reported. A competition experiment was conducted by incubating cells that overexpressed either the KDR receptor or the FLT-1 receptor with fixed amounts of $^{125}$I-labeled human VEGF or VEGF-E and then adding increasing amounts of unlabeled human VEGF or VEGF-E. The investigators reported that VEGF-E selectively bound KDR receptor as compared to FLT-1. [Ogawa et al. *J. Biological Chem.* 273:31273–31281 (1998)].

Meyer et al., *EMBO J.*, 18:363–374 (1999), have also identified a member of the VEGF family which is referred to as VEGF-E. The VEGF-E molecule reported by Meyer et al. was identified in the genome of Orf virus strain D1701. In vitro, the VEGF-E was found to stimulate release of tissue factor and stimulate proliferation of vascular endothelial cells. In a rabbit in vivo model, the VEGF-E stimulated angiogenesis in the rabbit cornea. Analysis of the binding properties of the VEGF-E molecule reported by Meyer et al., in certain assays revealed the molecule selectively bound to the KDR receptor as compared to the FLT-1 receptor.

Olofsson et al., *Proc. Natl. Acad. Sci.*, 95:11709–11714 (1998) report that a protein referred to as "VEGF-B" selectively binds FLT-1. The investigators disclose a mutagenesis experiment wherein the Asp63, Asp64, and Glu67 residues in VEGF-B were mutated to alanine residues. Analysis of the binding properties of the mutated form of VEGF-B revealed that the mutant protein exhibited a reduced affinity to FLT-1.

VEGF contains two sites that are responsible respectively for binding to the KDR (kinase domain region) and FLT-1 (FMS-like tyrosine kinase) receptors. These receptors are believed to exist primarily on endothelial (vascular) cells. Recently, Soker et al. identified another VEGF receptor that has a sequence identical to neuropilin. Soker et al., *Cell,* 92:735–745 (1998). This receptor bound to $VEGF_{165}$ and placental growth factor-2 (PLGF-2) but not to $VEGF_{121}$. Soker et al., supra; Migdal et al., *J. Biol. Chem.* 273: 22272–22278 (1998).

VEGF production increases in cells that become oxygen-depleted as a result of, for example, trauma and the like, thereby allowing VEGF to bind to the respective receptors to trigger the signaling pathways that give rise to a biological response. For example, the binding of VEGF to such receptors may lead to increased vascular permeability, causing cells to divide and expand to form new vascular pathways—i.e., vasculogenesis and angiogenesis. [See, e.g., Malavaud et al., *Cardiovascular Research,* 36:276–281 (1997)]. It is reported that VEGF-induced signaling through the KDR receptor is responsible for the mitogenic effects of VEGF and possibly, to a large extent, the angiogenic activity of VEGF. [Waltenberger et al., *J. Biol. Chem.,* 269:26988–26995 (1994)]. The biological role(s) of FLT-1, however, is less well understood.

The sites or regions of the VEGF protein involved in receptor binding have been identified and found to be proximately located. [See, Weismann et al., *Cell,* 28:695–704 (1997); Muller et al., *Proc. Natl. Acad. Sci.,* 94:7192–7197 (1997); Muller et al., *Structure,* 5:1325–1338 (1997); Fuh et al., *J. Biol. Chem.,* 273:11197–11204 (1998)]. The KDR receptor has been found to bind VEGF predominantly through the sites on a loop which contains arginine (Arg or R) at position 82 of VEGF, lysine (Lys or K) at position 84, and histidine (His or H) at position 86. The FLT-1 receptor has been found to bind VEGF predominantly through the sites on a loop which contains aspartic acid (Asp or D) at position 63, glutamic acid (Glu or E) at position 64, and glutamic acid (Glu or E) at position 67. [Keyt et al., *J. Biol. Chem.,* 271:5638–5646 (1996)]. Based on these findings, the wild type VEGF protein has been used as the starting point for introduction of mutations in specific receptor-binding sites, in attempts to create VEGF variants selectively bind to one receptor such as KDR. Keyt et al., supra; Shen et al. (1998) *J. Biol. Chem.* 273:29979–29985. The resulting VEGF variants showed moderate receptor selectivity. More recently, based on the crystal structure of VEGF and functional mapping of the KDR binding site of VEGF, it has further been found that VEGF engages KDR receptors using two symmetrical binding sites located at opposite ends of the molecule. Each site is composed of two "hot spots" for binding that consist of residues from both subunits of the VEGF homodimer. Muller et al., *Structure,* 5:1325–1338 (1997). Two of these binding determinants are located within the dominant hot spot on a short, 3-stranded beta-sheet that is conserved in transforming growth factor beta2 (TGF-beta) and platelet-derived growth factor (PDGF).

Recent studies report that endothelium-derived nitric oxide (NO) and endothelial NO synthase (eNOS) may play an important role in various VEGF-induced activities. NO is believed to be an important mediator of endothelial function and a regulator of vascular homeostasis, platelet aggregation, and angiogenesis. Busse and Flemming (1996) *J. Vasc. Res.* 33:181–194. NO is produced from conversion of L-arginine to citrulline by NO-synthase, an enzyme which consists of 3 isoforms denominated endothelial nitric oxide synthase (eNOS), inducible NOS (iNOS) and neuronal NOS (nNOS). Nathan and Xie (1994) *J. Biol. Chem.* 269:13725–13728. VEGF has been shown to induce rapid release of NO from rabbit, pig, bovine and human vascular endothelial cells. (see, e.g., vanderZee et al., *Circulation,* 95:1030–1037 (1997); Parenti et al., *J. Biol. Chem.,* 273: 4220–4226 (1998); Morbidelli et al., *Am. J. Physiol.,* 270: H411–H415 (1996); Papapetropoulis et al., *J. Clin. Invest.,* 100:3131–3139 (1997); Kroll et al., *Biochem. Biophys. Res. Comm.,* 252:743–746 (1998); Hood et al., *Am. J. Phys.,* 274:H1054–H1058 (1998)). In an in vitro assay, VEGF was found to stimulate human endothelial cells to grow in a NO-dependent manner and promote the NO-dependent formation of vessel-like structures in the 3-D collagen gel model (Papapetropoulis et al., supra). Conversely, eNOS inhibitors were reported to inhibit VEGF-induced mitogenic and angiogenic effects. (Papapetropoulis et al., supra). In certain in vivo studies, inactivation of eNOS expression impaired VEGF-induced angiogenesis in an eNOS knockout mouse model. (Murohara et al., *J. Clin. Invest.,* 101:2567–2578 (1998); Ziche et al., *J. Clin. Invest.,* 99:2625–2634 (1997); Rudic et al., *J. Clin. Invest.,* 101: 731–736 (1998)). Recently, Liu et al., *J. Biol. Chem.,* 274:15781–15785 (1999) reported that VEGF down-regulated an endogenous inhibitor of eNOS called Caveolin.

It has been shown that VEGF induces vasodilation in vitro in a dose-dependant fashion and produces transient tachicardia, hypotension and a decrease in cardiac output when injected intravenously in conscious, instrumented rats. Yang et al., *J. Cardiovasc. Pharmacol.,* 27:838–844 (1996) Such acute hemodynamic effects appear to be caused by a decrease in venous return, mediated primarily by endothelial cell-derived NO. Yang et al., supra; Hariawala et al., *J. Surg. Res.,* 63:77–82 (1996). Wu et al., *Am. J. Physiol.,* 271: H2735–H2739 (1996) describe that topical application of VEGF resulted in a transient and dose-dependent increase in albumin permeability in isolated coronary venules.

Inhibition of eNOS by L-NAME, in vivo, has been reported to result in an increase in mean arterial pressure (MAP) (Yang et.al., 1996 *Cardiovasc. Pharmacol.* 27:838–844; Sase et.al., 1997 *Trends J. Cardiovasc. Med.* 7:28–37) and a decrease in angiogenesis (Papapetropoulos et.al., 1997 *J.Clin. Invest.* 100:3131–3139). Genetically engineered mice lacking the eNOS gene showed impaired endothelium-dependent vasodilation, angiogenesis, and hypertension (Murohara et.al., 1998 *J.Clin. Invest.* 101: 2567–2578; Yang et. Al., 1996, supra), and over-expression of eNOS in mice by gene transfer was shown to increase nitric oxide production and significantly attenuated MAP and neointima formation (Sase et. al., supra; Drummond and Harrison, 1998, *J. Clin. Invest.* 102:2033–2044; Ohashi et.al., 1998 *J. Clin. Invest.* 102:2061–2071).

Although there have been a number of studies on the involvement of VEGF in short term release of NO and eNOS regulation, the chronic effect of VEGF on eNOS expression and/or activity has not been documented. Moreover, biological effects of sustained release of nitric oxide in treating or preventing vascular diseases in vivo have not been clearly demonstrated to date. This is due, in large part, to the fact that mammals can rapidly develop tolerance to certain agents exogenously administered as nitric oxide donors, making supplementation of nitric oxide difficult. (Drummond and Harrison, 1998, *J. Clin. Invest.* 102:2033–2044).

Up-regulation of eNOS expression by physiological or pharmacological approaches may provide a useful therapeutic approach to the treatment of diseases associated with endothelial cell dysfunction, for example, by increasing the production and sustained release of endogenous NO.

SUMMARY OF THE INVENTION

The present invention is based on the observation that prolonged VEGF treatment effectively up-regulates eNOS expression and activity, thereby enhancing sustained nitric oxide production, and that the eNOS upregulation by VEGF requires the VEGF-KDR receptor, activation of the KDR-associated tyrosine kinase (TK) and a downstream PKC-dependent pathway. Modulation of eNOS expression/activity is clinically useful, for example, in the treatment of disorders characterized by endothelial cell dysfunction including eNOS dysfunction and/or defects in nitric oxide production.

Therefore, in one embodiment, the invention provides as claimed a method of treating disorders in mammals wherein nitric oxide is an important regulator, such as hypertension, diabetes, atherosclerosis, thrombosis, angina and heart failure, by modulating eNOS expression or activity, for example, by the administration of an effective amount of VEGF, a receptor-selective VEGF variant, or an agent or molecule which acts as an agonist of VEGF receptor activation.

In another embodiment, the invention provides a method for protecting a mammal from conditions associated with endothelium dysfunction by providing VEGF or VEGF receptor agonist.

In yet another embodiment, the invention provides a method of stimulating a sustained production of endogenous NO in an endothelial cell by providing a receptor selective VEGF variant. Preferably, a KDR selective VEGF variant is used for specifically binding the KDR receptor, which in turn activates the pathway leading to the upregulation of eNOS and sustained NO production.

BRIEF DESCRIPTION OF THE DRAWINGS

FIG. 1A is a representative Western blot showing inducement of a time-dependent increase in eNOS expression by VEGF treatment. The arrow indicates eNOS. FIG. 1B is a bar diagram showing densitometry analysis of eNOS levels (means±SD, n=3). FIG. 1C is a bar diagram illustrating the chronic effect of VEGF on eNOS activity, as expressed by the activity ratio of VEGF-treated cells (after 2-day VEGF exposure) over untreated controls (at Day 0) (means±SD, n=3). FIG. 1D is a bar diagram illustrating the acute effect of VEGF on eNOS activity, as expressed by the percentage of activity increases of the VEGF-treated cells (treated for 0 to 60 min) over the untreated control.

FIG. 3A is a bar diagram showing that VEGF$_{165}$, VEGF$_{110}$, and a KDR selective binding variant ("KDR-sel") induce eNOS up-regulation, whereas FLT-1 receptor selective variants ("FLT-1-sel" and PLGF) did not. FIG. 3B is a Western blot showing VEGF-induced eNOS up-regulation in KDR-transfected PAE cells but not in FLT-1 containing PAE cells. FIG. 3C is a Western blot showing dose-dependent prevention of VEGF-induced eNOS up-regulation by KDR tyrosine kinase selective inhibitor SU1498. Arrows indicate eNOS.

FIG. 4A is a Western blot showing the effects on eNOS expression in ACE cells treated with VEGF in combination with various specific inhibitors of tyrosine kinase, PLC-gamma or PKC. FIG. 4B is a bar diagram illustrating analysis of eNOS levels by densitometry.

FIG. 5A is a Western blot showing that VEGF treatment resulted in a rapid re-distribution of PKC- alpha, gamma and epsilon from cytosolic to membrane fractions. FIG. 5B shows that VEGF increased PKC activity. FIG. 5C shows that activation of PKC with PMA increased eNOS levels.

DETAILED DESCRIPTION OF THE INVENTION

A. Definitions

Figure 1A:
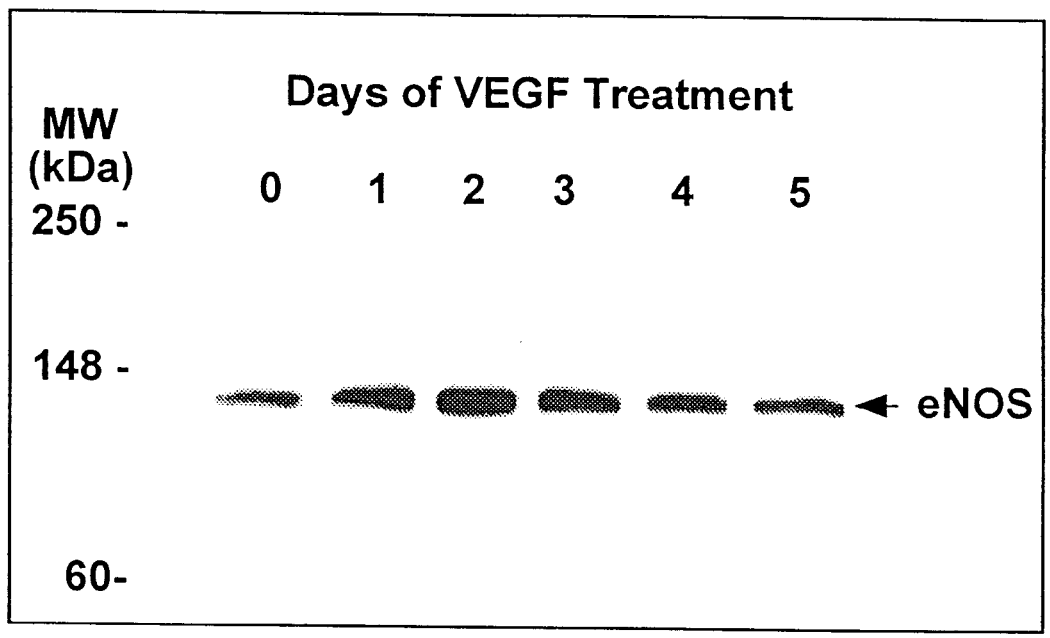
FIGS. 1A–1D depict the eNOS upregulation activity of VEGF.

The terms "VEGF" and "native VEGF" as used herein refer to the 165- amino acid vascular endothelial cell growth factor and related 121-, 189-, and 206- amino acid vascular endothelial cell growth factors, as described by Leung et al., *Science*, 246:1306 (1989), and Houck et al., *Mol. Endocrin.*, 5:1806 (1991), together with the naturally occurring allelic and processed forms thereof. The terms "VEGF" and "native VEGF" are also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8–109)," "VEGF (1–109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and FLT-1 receptors comparable to native VEGF.

The term "VEGF variant" as used herein refers to a VEGF polypeptide which includes one or more amino acid mutations in the native VEGF sequence and preferably, has selective binding affinity for either the KDR receptor or the FLT-1 receptor. In one embodiment, the VEGF variant includes one or more amino acid mutations in any one of positions 17 to 25 and/or 63 to 66 of the native VEGF sequence. Optionally, the one or more amino acid mutations include amino acid substitution(s). Optionally, VEGF variants include one or more amino acid mutations and exhibit binding affinity to the KDR receptor which is equal or greater than the binding affinity to the KDR receptor by native VEGF, and preferably, exhibit less binding affinity to the FLT-1 receptor than the binding affinity of native VEGF for FLT-1. When binding affinity of the VEGF variant for the KDR receptor is approximately equal (unchanged) or greater than (increased) as compared to native VEGF, and the binding affinity of the VEGF variant for the FLT-1 receptor is less than or nearly eliminated (as compared to native VEGF), the binding affinity of the VEGF variant is "selective" for the KDR receptor. Alternatively, the VEGF variants include one or more amino acid mutations and exhibit binding affinity to the FLT-1 receptor which is equal or greater than the binding affinity to the FLT-1 receptor by native VEGF, and preferably, exhibit less binding affinity to the KDR receptor than the binding affinity of native VEGF for KDR. When binding affinity of the VEGF variant for the FLT-1 receptor is approximately equal (unchanged) or greater than (increased) as compared to native VEGF, and the binding affinity of the VEGF variant for the KDR receptor is less than or nearly eliminated (as compared to native VEGF), the binding affinity of the VEGF variant is "selective" for the FLT-1 receptor. Preferred VEGF variants of the invention will have at least 10-fold less binding affinity to FLT-1 receptor (as compared to native VEGF), and even more preferably, will have at least 100-fold less binding affinity to FLT-1 receptor (as compared to native VEGF). The respective binding affinity of the VEGF variant for KDR or FLT-1 may be determined by ELISA, RIA, and/or BIAcore assays, known in the art and described further in the Examples below. Preferred VEGF variants of the invention will also exhibit activity in KIRA assays reflective of the capability to induce phosphorylation of the KDR receptor. Preferred VEGF variants of the invention will additionally or alternatively induce endothelial cell proliferation (which can be determined by known art methods such as the HUVEC proliferation assay). Induction of endothelial cell proliferation is presently believed to be the result of signal transmission by the KDR receptor.

For purposes of shorthand designation of VEGF variants described herein, it is noted that numbers refer to the amino acid residue position along the amino acid sequence of the putative native VEGF (provided in Leung et al., supra and Houck et al., supra.). Amino acid identification uses the single-letter alphabet of amino acids, i.e.,

| Asp | D | Aspartic acid | Ile | I | Isoleucine |
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

The term "VEGF receptor" as used herein refers to a cellular receptor for VEGF, ordinarily a cell-surface receptor found on vascular endothelial cells, as well as fragments and variants thereof which retain the ability to bind VEGF (such as fragments or truncated forms of the extracellular domain). One example of a VEGF receptor is the fms-like tyrosine kinase (FLT or FLT-1), a transmembrane receptor in the tyrosine kinase family. The term "FLT-1 receptor" used in the application refers to the VEGF receptor described, for instance, by DeVries et al., Science, 255:989 (1992); and Shibuya et al., Oncogene, 5:519 (1990). The full length FLT-1 receptor comprises an extracellular domain, a transmembrane domain, and an intracellular domain with tyrosine kinase activity. The extracellular domain is involved in the binding of VEGF, whereas the intracellular domain is involved in signal transduction. Another example of a VEGF receptor is the KDR receptor (also referred to as FLK-1). The term "KDR receptor" used in the application refers to the VEGF receptor described, for instance, by Matthews et al., Proc. Nat. Acad. Sci., 88:9026 (1991); and Terman et al., Oncogene, 6:1677 (1991); Terman et al., Biochem. Biophys. Res. Commun., 187:1579 (1992).

A receptor "agonist" is an agent that has affinity to and activate a receptor normally activated by a naturally occurring ligand, thus triggering a biochemical response. Generally, the receptor activation capability of the agonist will be at least qualitatively similar (and may be essentially quantitatively similar) to a native ligand of the receptor. Non-limiting examples of a receptor agonist include ligand variant, antibody against the receptor and antibody against the receptor-ligand complex.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851–6855 (1984)).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

"Chronic" administration refers to administration of the agent(s) in a continuous mode as opposed to an acute mode, so as to maintain the initial therapeutic effect (activity) for an extended period of time. Intermittent administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cows, horses, sheep, pigs, etc. Preferably, the mammal is human.

Administration "in combination with" one or more further therapeutic agents includes simultaneous (concurrent) and consecutive administration in any order.

Pathologic conditions and disorders "associated with" NO or "characterized by" eNOS dysfunction and/or wherein NO is an "important regulator" are those conditions and disorders where nitric oxide insufficiency or excess is correlated with disease. Such disorders and conditions include, for example, hypertension, diabetes, thrombosis, angina, atherosclerosis, and heart failure, wherein nitric oxide levels in mammalian cells or tissues are present in insufficient quantities as compared to normal or healthy mammalian cells or tissues. Further applications in which the use of VEGF will be beneficial include the use of VEGF to increase eNOS or NO production prior to, concurrent with or subsequent to angioplasty to prevent restenosis or neointima formation.

The terms "hypertension" or "hypertensive condition" as used herein refer to a physiological state or syndrome in mammals typically characterized by increased peripheral vascular resistance or cardiac output, or both. Clinically, "hypertension" or "hypertensive condition" may optionally be indicated by blood pressure measurements equal to or greater than approximately 140 mm Hg systolic and approximately 90 mm Hg Hg diastolic. Hypertension is further characterized in Oates, "Antihypertensive Agents and the Drug Therapy of Hypertension", Chapter 33, Goodman and Gilman, 9$^{th}$ Edition, pages 780–781. The terms as used herein include acute and chronic hypertensive conditions.

As used herein, "modulation" of eNOS activity is used in a broad sense and refers to the ability to induce or enhance, inhibit or decrease, or maintain eNOS protein expression and/or activity.

B. Mode(s) for Carrying out the Invention

In one aspect, the invention provides methods for treating a NO associated disorder or condition such as hypertension, diabetes, thrombosis, angina, heart failure or atherosclerosis. Applicants have observed that some coronary artery disease patients (humans) treated with rhVEGF (either by intracoronary or intravenous infusion administration at 0.05 microgram/Kg body weight/minute) can have a dose-rate dependent reduction in mean arterial pressure. This type of reduction in mean arterial pressure was acute and typically was observed during the first 20 minutes of infusion. In contrast, some cancer patients (humans) treated with recombinant humanized monoclonal antibodies against VEGF can have a dose-dependent increase in mean arterial pressure. Such increase in mean arterial pressure is believed to be due to the neutralization of endogenous VEGF. It is further believed that the blocking or neutralization of VEGF may down-regulate eNOS production or decrease endothelial cell function, affecting the vascular homeostasis and resulting in an increase in blood pressure. Accordingly, VEGF, or molecules modulating VEGF receptor activation, as described herein may be employed to treat conditions or disorders associated with NO or eNOS dysfunction.

The invention also provides methods for protecting a mammalian subject from conditions associated with endothelium dysfunction such as thrombosis. Early results from a VIVA clinical trial (VEGF in Ischemia for Vascular Angiogenesis) indicate that VEGF treated angina patients show trends of improvement compared to placebo group, in such measures as angina class, angina frequency, and treadmill times at a prolonged time point. It is contemplated that the VEGF or VEGF receptor agonist of the invention provides important vascular protective effects through up-regulating eNOS and NO in endothelial cells. The prolonged treatment of target subject with VEGF or VEGF receptor agonist according to the invention provides chronic effects on eNOS upregulation and sustained production of NO, which are more beneficial for therapeutic treatments or prophylactic measures wherein a sustained level of NO is desired. By boosting the endogenous NO production via upregulating the eNOS enzyme, the methods of the invention are also applicable in treatment or prevention wherein the patients currently rely on exogenous nitrate sources, such as angina patients. Luscher TF (1992) *Br. J. Clin. Pharmacol.* 34 Suppl. 1:29S–35S.

The invention further provides methods of using a KDR selective VEGF variant for stimulating a sustained production of endogenous NO in an endothelial cell. Native VEGF is a pleiotropic growth factor having multiple biological effects in regulating physiological and pathological vascular functions. When used in vitro or in vivo, native VEGF may cause unwanted adverse effects in addition to the targeted function(s), a problem often complicating the therapeutic applications of VEGF. Accordingly, the invention provides methods of using the receptor-selective variants as alternative therapeutic agents that may have fewer side effects than the native VEGF protein.

In one aspect, the VEGF or VEGF receptor agonist of the invention is capable of upregulating the expression level of eNOS in an endothelial cell. Without being bound to particular mechanisms, the eNOS expression level can be upregulated by increasing the transcription of the eNOS gene, or alternatively, by preventing the degradation of the transcribed eNOS mRNAs, or the combination of both. In another aspect, the VEGF or VEGF receptor agonist of the invention is capable of upregulating the activity of endogenous eNOS. It has been shown that a number of proteins are associated with eNOS and regulate the eNOS activity via protein—protein interactions. For example, it has been shown that caveolin and PLC-γ decrease the eNOS activity, whereas HSP-70 and HSP-90 increase the eNOS activity, when associated with eNOS. Applicants have observed that in cultured endothelial cells, VEGF treatment induces dissociation of caveolin and PLC-γ from eNOS and increase association of eNOS to HSP-70 and HSP-90. Furthermore, prolonged VEGF treatment is shown to reduce the phosphotyrosine level of eNOS, another indication of eNOS activation (Example 14).

VEGF and VEGF variants for use in the disclosed methods may be prepared by a variety of methods well known in the art. Preferably, the VEGF employed in the methods of the present invention comprises recombinant VEGF$_{165}$. Amino acid sequence variants of VEGF can be prepared by mutations in the VEGF DNA. Such variants include, for example, deletions from, insertions into or substitutions of residues within the amino acid sequence shown in Leung et al., supra and Houck et al., supra. Any combination of deletion, insertion, and substitution may be made to arrive at the final construct having the desired activity. Obviously, the mutations that will be made in the DNA encoding the variant must not place the sequence out of reading frame and preferably will not create complementary regions that could produce secondary mRNA structure [see EP 75,444A].

The VEGF variants optionally are prepared by site-directed mutagenesis of nucleotides in the DNA encoding the native VEGF or phage display techniques, thereby producing DNA encoding the variant, and thereafter expressing the DNA in recombinant cell culture.

While the site for introducing an amino acid sequence variation is predetermined, the mutation per se need not be predetermined. For example, to optimize the performance of a mutation at a given site, random mutagenesis may be conducted at the target codon or region and the expressed VEGF variants screened for the optimal combination of desired activity. Techniques for making substitution mutations at predetermined sites in DNA having a known sequence are well-known, such as, for example, site-specific mutagenesis.

Preparation of the VEGF variants described herein is preferably achieved by phage display techniques, such as those described in the Examples.

After such a clone is selected, the mutated protein region may be removed and placed in an appropriate vector for protein production, generally an expression vector of the type that may be employed for transformation of an appropriate host.

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length as well as intrasequence insertions of single or multiple amino acid residues. Intrasequence insertions (i.e., insertions within the native VEGF sequence) may range generally from about 1 to 10 residues, more preferably 1 to 5. An example of a terminal insertion includes a fusion of a signal sequence, whether heterologous or homologous to the host cell, to the N-terminus to facilitate the secretion from recombinant hosts.

Additional VEGF variants are those in which at least one amino acid residue in the native VEGF has been removed and a different residue inserted in its place. Such substitutions may be made in accordance with those shown in Table 1.

TABLE 1

| Original Residue | Exemplary Substitutions |
| --- | --- |
| Ala (A) | gly; ser |
| Arg (R) | lys |
| Asn (N) | gln; his |

TABLE 1-continued

| Original Residue | Exemplary Substitutions |
| --- | --- |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu; tyr |
| Ser (S) | thr |
| Thr (T) | ser |
| Trp (W) | tyr |
| Tyr (Y) | trp; phe |
| Val (V) | ile; leu |

Changes in function or immunological identity may be made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in the VEGF variant properties will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; (e) a residue having an electronegative side chain is substituted for (or by) a residue having an electropositive charge; or (f) a residue having a bulky side chain, e.g., phenylalanine, is substituted for (or by) one not having such a side chain, e.g., glycine.

The effect of the substitution, deletion, or insertion may be evaluated readily by one skilled in the art using routine screening assays. For example, a phage display-selected VEGF variant may be expressed in recombinant cell culture, and, optionally, purified from the cell culture. The VEGF variant may then be evaluated for KDR or FLT-1 receptor binding affinity and other biological activities, such as those disclosed in the present application. The binding properties or activities of the cell lysate or purified VEGF variant can be screened in a suitable screening assay for a desirable characteristic. For example, a change in the immunological character of the VEGF variant as compared to native VEGF, such as affinity for a given antibody, may be desirable. Such a change may be measured by a competitive-type immunoassay, which can be conducted in accordance with techniques known in the art. The respective receptor binding affinity of the VEGF variant may be determined by ELISA, RIA, and/or BIAcore assays, known in the art and described further in the Examples below. Preferred VEGF variants of the invention will also exhibit activity in KIRA assays (such as described in the Examples) reflective of the capability to induce phosphorylation of the KDR receptor. Preferred VEGF variants of the invention will additionally or alternatively induce endothelial cell proliferation (which can be determined by known art methods such as the HUVEC proliferation assay in the Examples). In addition to the specific VEGF variants disclosed herein, the VEGF variants described in Keyt et al., *J. Biol. Chem.*, 271:5638–5646 (1996) are also contemplated for use in the present invention.

VEGF variants may be prepared by techniques known in the art, for example, recombinant methods. Isolated DNA used in these methods is understood herein to mean chemically synthesized DNA, cDNA, chromosomal, or extrachromosomal DNA with or without the 3'- and/or 5'-flanking regions. Preferably, the VEGF variants herein are made by synthesis in recombinant cell culture.

For such synthesis, it is first necessary to secure nucleic acid that encodes a VEGF or VEGF variant. DNA encoding a VEGF molecule may be obtained from bovine pituitary follicular cells by (a) preparing a cDNA library from these cells, (b) conducting hybridization analysis with labeled DNA encoding the VEGF or fragments thereof (up to or more than 100 base pairs in length) to detect clones in the library containing homologous sequences, and (c) analyzing the clones by restriction enzyme analysis and nucleic acid sequencing to identify full-length clones. If full-length clones are not present in a cDNA library, then appropriate fragments may be recovered from the various clones using the nucleic acid sequence information disclosed herein for the first time and ligated at restriction sites common to the clones to assemble a full-length clone encoding the VEGF. Alternatively, genomic libraries will provide the desired DNA.

Once this DNA has been identified and isolated from the library, it is ligated into a replicable vector for further cloning or for expression.

In one example of a recombinant expression system, a VEGF-encoding gene is expressed in a cell system by transformation with an expression vector comprising DNA encoding the VEGF. It is preferable to transform host cells capable of accomplishing such processing so as to obtain the VEGF in the culture medium or periplasm of the host cell, i.e., obtain a secreted molecule.

"Transfection" refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

"Transformation" refers to introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, *Proc. Natl. Acad. Sci.* (USA), 69: 2110 (1972) and Mandel et al., *J. Mol. Biol.*, 53: 154 (1970), is generally used for prokaryotes or other cells that contain substantial cell-wall barriers. For mammalian cells without such cell walls, the calcium phosphate precipitation method of Graham and van der Eb, *Virology*, 52: 456–457 (1978), is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci.* (USA), 76: 3829 (1979). However, other methods for introducing DNA into cells such as by nuclear injection or by protoplast fusion may also be used.

The vectors and methods disclosed herein are suitable for use in host cells over a wide range of prokaryotic and eukaryotic organisms.

In general, of course, prokaryotes are preferred for the initial cloning of DNA sequences and construction of the vectors useful in the invention. For example, *E. coli* K12 strain MM 294 (ATCC No. 31,446) is particularly useful. Other microbial strains that may be used include *E. coli* strains such as *E. coli* B and *E. coli* X1776 (ATCC No. 31,537). These examples are, of course, intended to be illustrative rather than limiting.

Prokaryotes may also be used for expression. The aforementioned strains, as well as *E. coli* strains W3110 (F-, lambda-, prototrophic, ATCC No. 27,325), K5772 (ATCC No. 53,635), and SR101, bacilli such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site as well as marking sequences that are capable of providing phenotypic selection in transformed cells. For example, *E. coli* is typically transformed using pBR322, a plasmid derived from an *E. coli* species (see, e.g., Bolivar et al., *Gene*, 2:95 (1977)]. pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems [Chang et al., *Nature*, 375:615 (1978); Itakura et al., *Science*, 198:1056 (1977); Goeddel et al., *Nature*, 281:544 (1979)] and a tryptophan (trp) promoter system [Goeddel et al., *Nucleic Acids Res.*, 8:4057 (1980); EPO Appl. Publ. No. 0036,776]. While these are the most commonly used, other microbial promoters have been discovered and utilized, and details concerning their nucleotide sequences have been published, enabling a skilled worker to ligate them functionally with plasmid vectors [see, e.g., Siebenlist et al., *Cell*, 20:269 (1980)].

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in *Saccharomyces*, the plasmid YRp7, for example [Stinchcomb et al., *Nature*, 282:39 (1979); Kingsman et al., *Gene*, 7:141 (1979); Tschemper et al., *Gene*, 10:157 (1980)], is commonly used. This plasmid already contains the trp1 gene that provides a selection marker for a mutant strain of yeast lacking the ability to grow in tryptophan, for example, ATCC No. 44,076 or PEP4-1 [Jones, *Genetics*, 85:12 (1977)]. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland et al., *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication [Fiers et al., *Nature*, 273:113 (1978)]. Smaller or larger SV40 fragments may also be used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both VEGF and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci. (USA)*, 77:4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

Construction of suitable vectors containing the desired coding and control sequences employs standard ligation techniques. Isolated plasmids or DNA fragments are cleaved, tailored, and religated in the form desired to prepare the plasmids required.

If blunt ends are required, the preparation may be treated for 15 minutes at 15° C. with 10 units of Polymerase I (Klenow), phenol-chloroform extracted, and ethanol precipitated.

Size separation of the cleaved fragments may be performed using, by way of example, 6 percent polyacrylamide gel described by Goeddel et al., *Nucleic Acids Res.*, 8:4057 (1980).

To confirm correct sequences were constructed in plasmids, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.*, 9:309 (1981) or by the method of Maxam et al., *Methods of Enzymology*, 65:499 (1980).

After introduction of the DNA into the mammalian cell host and selection in medium for stable transfectants, amplification of DHFR-protein-coding sequences is effected by growing host cell cultures in the presence of approximately 20,000–500,000 nM concentrations of methotrexate (MTX), a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Antibodies against the KDR receptor or FLT-1 receptor may also be employed in the methods of the present invention. Optionally, the KDR receptor or FLT-1 receptor antibody is a monoclonal antibody. Optionally, the KDR receptor antibody is an agonist antibody which, preferably, is capable of up-regulating eNOS levels and/or activity. In a hybridoma method for preparing such monoclonal antibodies, a mouse or other appropriate host animal is immunized with antigen by subcutaneous, intraperitoneal, or intramuscular routes to elicit lymphocytes that produce or are capable of producing antibodies that will specifically bind to the protein(s) used for immunization. Alternatively, lymphocytes may be immunized in vitro. Lymphocytes then are fused with myeloma cells using a suitable fusing agent, such as polyethylene glycol, to form a hybridoma cell. Goding,

*Monoclonal Antibodies: Principles and Practice*, pp. 59–103 (Academic Press, 1986).

The antigen may be KDR receptor or FLT-1 receptor or optionally, a fragment or portion or epitope or variant thereof having one or more amino acid residues that participate in the binding of hVEGF to its receptors. For example, immunization with an extracellular domain sequence of KDR may especially be useful in producing antibodies that are agonists or antagonists of hVEGF, since it is region(s) within or spanning the extracellular domain that are involved in hVEGF binding. The use of chimeric, anti-idiotypic, humanized or human antibodies against KDR or FLT-1 are contemplated for use in the present invention and may be prepared using techniques known to the skilled artisan.

The VEGF receptor monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The VEGF receptor antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The VEGF receptor antibodies may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1): 86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

In one embodiment, the therapeutic methods of the present invention include administering VEGF to a mammal to treat hypertension. Hypertension is a relatively common cardiovascular disease in mammals. For instance, elevated arterial pressures can cause pathological changes in the vasculature or hypertrophy of the left ventricle of the heart. Hypertension can result in stroke in some mammals, as well as lead to disease of the coronary arteries or myocardial infarction.

The VEGF of the invention may be formulated and dosed in a fashion consistent with good medical practice taking into account the specific hypertensive condition to be treated, the condition of the individual patient, the site of delivery of the agent, the method of administration, and other factors known to practitioners. "An effective amount" of VEGF includes amounts that prevent, lessen the worsening of, alleviate, or cure the condition being treated or symptoms thereof. Optionally, "an effective amount" of VEGF is that amount which enhances or up-regulates nitric oxide production in the mammal. Optionally, the VEGF may be used to treat acute conditions of hypertension, as well as for treating patients suffering from chronic hypertension.

The VEGF may be prepared for storage or administration by mixing the VEGF having the desired degree of purity with physiologically acceptable carriers, excipients, or stabilizers. Suitable carrier vehicles and their formulation, inclusive of other human proteins, for example, human serum albumin, are described, for example, in *Remington's Pharmaceutical Sciences,* 16th ed., 1980, Mack Publishing Co., edited by Oslo et al. Typically, an appropriate amount of a pharmaceutically-acceptable salt is used in the formulation to render the formulation isotonic. Examples of the carrier include buffers such as saline, Ringer's solution, and dextrose solution. The pH of the solution is preferably from about 5.0 to about 8.0. For example, if the VEGF is water soluble, it may be formulated in a buffer such as phosphate or other organic acid salt at a pH of about 7.0 to 8.0. If a VEGF is only partially soluble in water, it may be prepared as a microemulsion by formulating it with a nonionic surfactant such as Tween, Pluronics, or PEG, e.g., Tween 80, in an amount of 0.04–0.05% (w/v), to increase its solubility.

Further carriers include sustained release preparations which include the formation of microcapsular particles and implantable articles. Examples of sustained release preparations include, for example, semipermeable matrices of solid hydrophobic polymers, which matrices are in the form of shaped articles, e.g., films, liposomes or microparticles. A suitable material for this purpose is a polylactide, although other polymers of poly-(beta-hydroxycarboxylic acids), such as poly-D-(–)-3-hydroxybutyric acid [EP 133,988A], can be used. Other biodegradable polymers such as, for example, poly(lactones), poly(acetals), poly(orthoesters), or poly(ortho-carbonates) are also suitable.

For examples of sustained release compositions, see U.S. Pat. No. 3,773,919, EP 58,481A, U.S. Pat. No. 3,887,699, EP 158,277A, Canadian Patent No. 1176565, Sidman et al., *Biopolymers,* 22:547 (1983), and Langer et al., *Chem. Tech.,* 12:98 (1982).

It will be apparent to those persons skilled in the art that certain carriers may be more preferable depending upon, for instance, the route of administration and concentration of the VEGF being administered.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates, including cellulose or its derivatives, glucose, mannose, or dextrins; chelating agents such as EDTA; and sugar alcohols such as mannitol or sorbitol. The use of excipients, carriers, stabilizers, or other additives may result in the formation of salts of the VEGF.

When selecting carriers, excipients, stabilizers, or other additives, the selected compound(s) and corresponding degradation products should be nontoxic and avoid aggravating the condition treated and/or symptoms thereof. This can be determined by routine screening in animal models of the target disorder or, if such models are unavailable, in normal animals.

The VEGF to be used for therapeutic administration should be sterile. Sterility is readily accomplished by filtration through sterile filtration membranes (e.g., 0.2 micron membranes). The VEGF ordinarily will be stored in lyophilized form or as an aqueous solution.

Administration to a mammal may be accomplished by injection (e.g., intravenous, intraperitoneal, subcutaneous, intramuscular) or by other methods such as infusion that ensure delivery to the bloodstream in an effective form. If the VEGF is to be used parenterally, therapeutic compositions containing the VEGF generally are placed into a container having a sterile access port, for example, an intravenous solution bag or vial having a stopper pierceable by a hypodermic injection needle.

Generally, where the condition permits, one may formulate and dose the VEGF for site-specific delivery.

In one aspect, the VEGF of the invention may be administered by intravenous infusion at a dose of approximately up to 0.05 microgram/Kg/minute for about 4 hours on a daily schedule. Such VEGF may be administered at 48 hour or 72 hour intervals. Optionally, the VEGF may be administered intramuscularly or subcutaneously in a sustained release formulation at a dose of approximately 0.25 to about 2.5 mg/Kg, preferably, approximately 0.3 to about 1.0 mg/Kg. Still further, the VEGF may be administered to the mammal via a plasmid or viral vector to provide a sustained expression of the VEGF gene product to improve endothelial cell function or eNOS expression. Also contemplated is the use of VEGF in stent implantation. Local delivery of VEGF coated STENT provides for local eNOS upregulation and is beneficial to, for example, inhibit restenosis after balloon injury, since NO is a potent antithrombotic agent and has also been shown to inhibit smooth muscle cell (SMC) proliferation and restenosis.

The VEGF of the invention can also be used in a topical application for treating indications such as wound healing. When applied topically, VEGF can upregulate local eNOS and or iNOS production so as to enhance healing and prevent infection. When used in a topical application, the VEGF can be suitably combined with additives, such as carriers, adjuvants, stabilizers, or excipients. As described above, when selecting additives for admixture with a VEGF, additives should be pharmaceutically acceptable and efficacious for their intended administration. Further, additives should not affect the activity of the VEGF. Examples of suitable topical formulations include ointments, creams, gels, or suspensions, with or without purified collagen. The compositions also may be impregnated into transdermal patches, plasters, and bandages, preferably in liquid or semi-liquid form.

A gel formulation having the desired viscosity may be prepared by mixing VEGF with a water-soluble polysaccharide, such as a cellulose derivative, or synthetic polymer, such as polyethylene glycol. The term "water soluble" as applied to the polysaccharides and polyethylene glycols is meant to include colloidal solutions and dispersions. In general, the solubility of, for example, cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, Li, Na, K, or Cs salts.

Examples of suitable polysaccharides include, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the VEGF held within it.

Preferably the polysaccharide is an etherified cellulose derivative, more preferably one that is well defined, purified, and listed in USP, for example, methylcellulose and the hydroxyalkyl cellulose derivatives, such as hydroxypropyl cellulose, hydroxyethyl cellulose, and hydroxypropyl methylcellulose. Most preferred herein is methylcellulose. For example, a gel formulation comprising methylcellulose preferably comprises about 2–5% methylcellulose and 300–1000 mg of VEGF per milliliter of gel. More preferably, the gel formulation comprises about 3% methylcellulose.

The polyethylene glycol useful for a gel formulation is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

It is within the scope hereof to combine the VEGF therapy with other novel or conventional therapies (e.g., growth factors such as aFGF, bFGF, PDGF, IGF, NGF, HGF, anabolic steroids, EGF or TGF-beta). It is not necessary that such co-treatment drugs be included per se in the compositions of this invention, although this will be convenient where such drugs are proteinaceous. Such admixtures are suitably administered in the same manner as the VEGF.

The afore-described formulations and modes of administration may also be utilized to administer other molecules which modulate VEGF receptor activity, such as VEGF receptor selective variants or VEGF receptor antibodies. Effective dosages and schedules for such administration may be determined empirically, and making such determinations is within the skill in the art.

The following examples are offered for illustrative purposes only and are not intended to limit the scope of the present invention in any way.

All patent and literature references cited in the present specification are hereby incorporated by reference in their entirety.

EXAMPLES

Commercially available reagents referred to in the Examples below were used according to manufacturer's instructions unless otherwise indicated. The source of those cells identified in the following examples, and throughout the specification, by ATCC accession numbers is the American Type Culture Collection, Manassas, Va.

Example 1

VEGF Up-Regulation of eNOS Expression

To study whether VEGF regulates eNOS expression, bovine adrenal cortex endothelial cells (ACE) cells were incubated with rhVEGF for 0–5 days. At the end of incubation, total cell lysates were prepared, and eNOS protein levels were determined by Western blot analysis.

Materials:

Recombinant human $VEGF_{165}$ ($rhVEGF_{165}$) was produced in *E. Coli* [see, Siemeister et al., *Biochem. Biophys. Res. Comm.*, 222:249–255 (1996); also available from R & D Systems]. The $VEGF_{110}$ heparin binding domain-deficient variant was made from $VEGF_{165}$ by limited proteolytic digestion with plasmin as described previously (Keyt et al., 1996, *J. Biol. Chem.*, 271:7788–7795).

VEGF receptor selective mutants FLT-sel (R82E/K84E/H86E, deficient in KDR binding) and KDR-sel (D63A/E64A/E67A, deficient in FLT-1 binding) were prepared using the MUTA-GENE® Phagemid in vitro mutagenesis kit as described previously (Keyt et al., 1996, J. Bio. Chem., 271:4538–5646). The heterodimeric form of recombinant human hepatocyte growth factor (HGF) was produced in and isolated from Chinese hamster ovary cells as previously described (Shen et al., 1997, *Am. J. Physiol.*, 272:L1115–L1120).

Recombinant human fibroblast growth factor (FGF) basic, recombinant human placental growth factor (PLGF), recombinant human transforming growth factor (TGF-beta1, TGF-beta2), and recombinant human epidermal growth factor (EGF) were purchased from R&D Systems, Inc. (Minneapolis, Minn.). Monoclonal anti-eNOS antibody was purchased from BIOMOL (Plymouth Meeting, Pa.). Monoclonal anti-PKC antibodies were purchased from Transduction Lab (Lexington, Ky.). SU1498 was purchased from CALBIOCHEM (San Diego, Calif.). PP1, PD98059, staurosporine, herbimycin A, genistein, phorbol 12-myristate 13-acetate (PMA), wortmannin, Ly294002, L-$N^G$-Nitroarginine methyl ester (L-NAME) were ordered from BIOMOL (Plymouth Meeting, Pa.). Sodium nitroprusside (SNAP) was from Sigma (St. Louis, Mo.). NOSdetect Assay kit was purchased from STRATAGENE (La Jolla, Calif.). L-[2,3,4,5-$^3$H]Arginine monohydrochloride was purchased from Amersham Phamacia Biotech. Geneticin (G480) was obtained from Life Technologies (Gaithersburg, Md.). All reagents were prepared as 1000× stock solution unless otherwise specified.

Cell Cultures:

Bovine adrenal cortex capillary endothelial cells (ACE) were prepared and maintained as previously described (Ferrara et.al., 1989 *Biochem. Biophys. Res. Commun.* 161: 851–858). Briefly, cells were plated onto 6-well tissue culture plates (Costar) and grown in low glucose Dulbecco's modified Eagle's medium, supplemented with 2 mM L-Glutamate (Life Technologies), 10% bovine calf serum (HyClone Lab., Inc.) and 100 µg/ml Penicillin/Streptomycin (Life Technologies). ACE cells were used between passages 4 and 8.

Porcine aorta endothelial (PAE) cells, and receptor transfected PAE cells (PAE/KDR and PAE/FLT-1) were provided by Napoleone Ferrara (Genentech, Inc.) and cultured in Ham's F-12 medium containing 10% FBS (for PAE), or plus 250 µg/ml G480 (for PAE/KDR and PAE/FLT-1).

For drug treatment, cells were incubated in the medium containing 10% FBS supplemented with VEGF or other drugs as specified. Medium was changed every 24 hours.

Western Blot Detection of eNOS:

The methods for cell lysis and Western blot (WB) have been described in Shen et al., 1998 *J. Biol. Chem.* 273: 29979–29985. A monoclonal anti-eNOS antibody was used at 1:2500 to probe eNOS protein. A secondary antibody conjugated with horseradish peroxidase (1:2500) (Zymed) and an enhanced chemiluminescent kit (Amershal Pharmacia Biotech) were used to visualize the eNOS immunoreactive bands. Multiple exposures of films were obtained to determine the optimal exposure time. The protein bands were scanned by a densitometer and the relative intensities were quantified using IMAGEQUANT® software (Molecular Dynamics).

eNOS Activity Assay:

The eNOS activity in ACE cells treated with or without rhVEGF for 2 days was determined by measuring the formation of [$^3$H]citrulline from [$^3$H]arginine. Briefly, ACE cells were homogenized in a buffer containing 25 mM Tris-HCl, pH 7.4, 1 mM EDTA and 1 mM EGTA, and then subjected to microcentrifugation at 14,000 rpm for 5 minutes. 50 μg of protein from the supernatants was incubated with 1 mM NADPH, 25 mM Tris-HCl, pH 7.4, 3 μM tetrahydrobiopterin (BH4), 1 mM flavin adenine dinucleotide (FAD), 1 μM flavin adenine mononucleotide, 0.1 μCi/ml of [$^3$H]arginine, and other cofactors (calcium and calmodulin) provided in the assay kit (STRATAGENE) at 37° C. for 45 minutes. The reaction was stopped with 50 mM HEPES, pH 5.5, 5 mM EDTA. Equilibrated resin, which binds to the arginine, was added to the reactions and then pipetted into spin cups. [$^3$H]citrulline, which is ionically neutral at pH 5.5, flowed through the cups completely and was then quantitated by scintillation counting.

Confluent ACE cells were incubated with 500 pM rhVEGF. Total cell lysates were prepared as described above. Equal amounts of protein were denatured under reducing conditions and separated in a 10% Novex mini gel and transferred to PVDF membrane. eNOS protein signals were visualized by ECL and quantified using densitometry. The eNOS activity in cells treated with or without VEGF for 2 days was assayed using a NOS detection kit from Stratagene according to the manufacturer's protocol.

CGMP Assay:

eNOS activity can also be determined by measuring the production of cyclic GMP (cGMP), a down-stream product following NO release as a result of eNOS activation. Papapetropoulis et al., supra. There are several commercial available cGMP assay kits, such as the one from BioMol. BioMol EIA cGMP kit is a competitive immunoassay for quantitative determination of cGMP in samples treated with 0.1 m HCl. The kit uses a polyclonal antibody to cGMP to bind, in a competitive manner, the cGMP in sample or an alkaline phosphatase molecule which has cGMP covalently attached to it. After incubation, the excess reagents are washed away and substrate added. Then enzyme reaction is stopped and the yellow color generated is read on a microplate reader at 405 nm. The intensity of the bound yellow color is inversely proportional to the concentration of cGMP in samples.

Figure 1B:
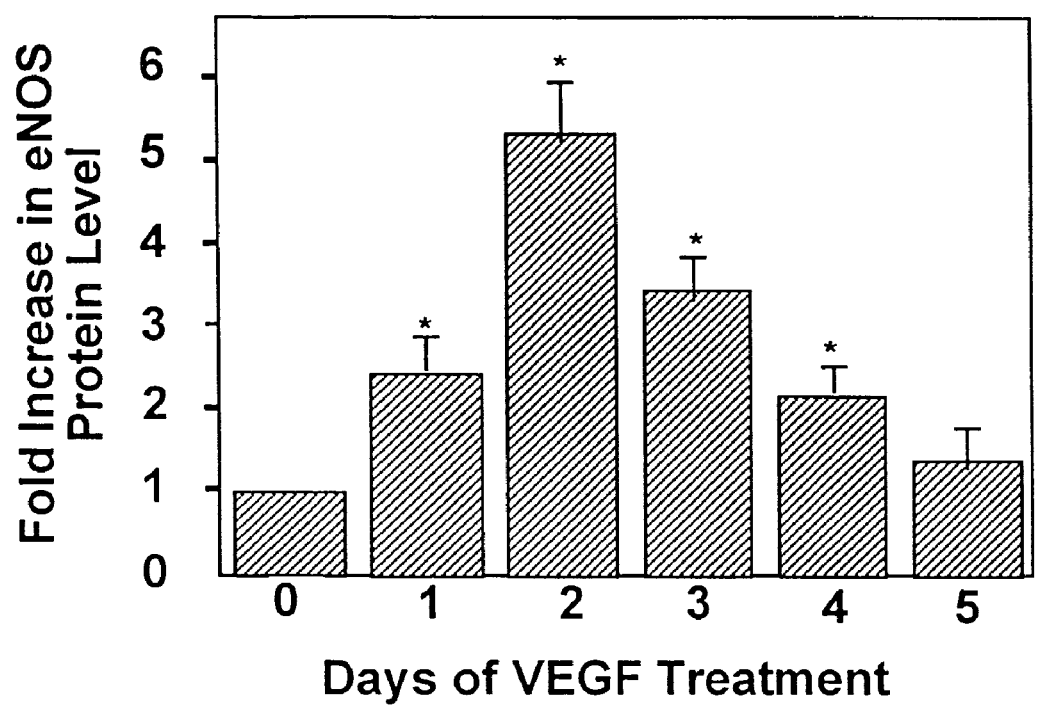

Results:

VEGF induced eNOS up-regulation in a dose-dependent manner with the maximal increase occurring following incubation with 500 pM VEGF (data not shown). FIG. 1A shows the results of a time-course experiment, indicating that prolonged VEGF treatment induced a transient increase in eNOS expression. The peak expression (5.5 fold) was observed at 2 days (48 hours) post exposure to 500 pM VEGF (FIG. 1B).

Figure 1C:
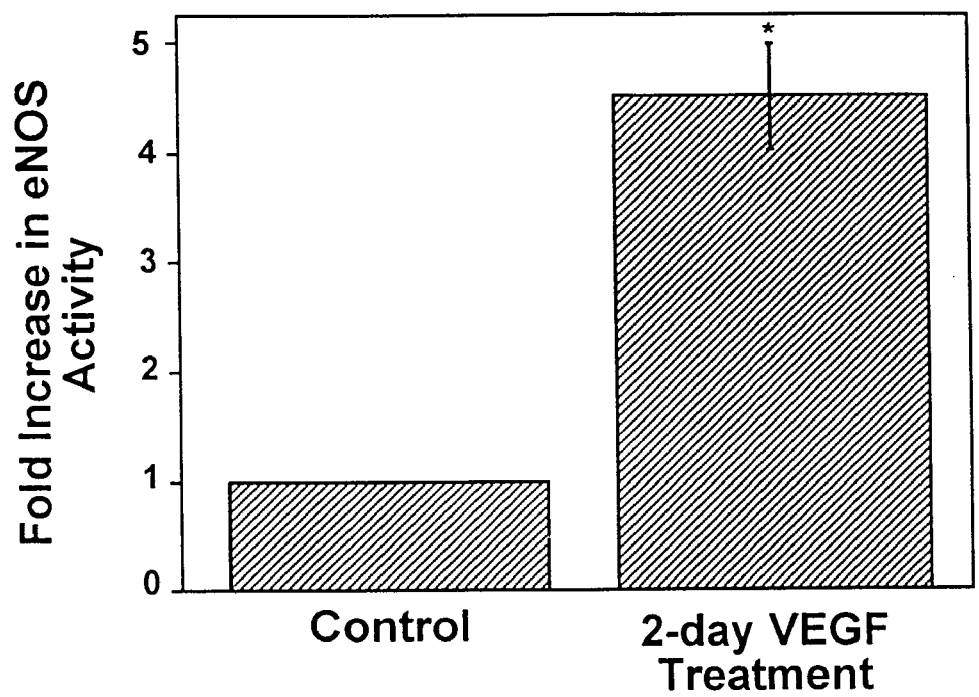
Figure 1D:
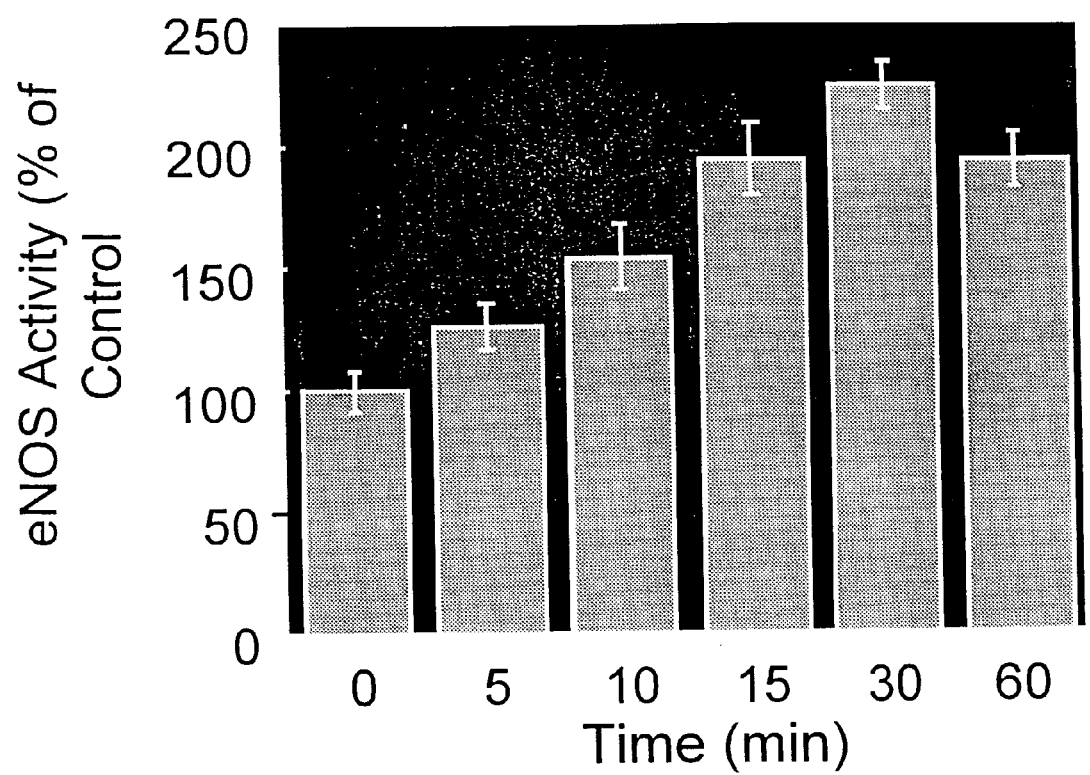

In addition, eNOS activity in cell lysates from cells incubated with or without VEGF for 0–60 min or 2 days was measured using a NOS DETECTION® kit. FIG. 1C shows that eNOS activity in VEGF-treated cells was about 5 fold greater than that in untreated control cells, which was proportional to the increased eNOS protein levels (5.5 fold). FIG. 1D shows that acute VEGF treatment (0–60 min) resulted in a time-dependent increase in eNOS activity.

The total NOS activity measured in ACE cells likely represents eNOS activity because (1) the assay measured $Ca^{+2}$ dependent NOS activity and (2) there was no detectable eNOS proteins by Western blot in either VEGF treated or untreated cells (data not shown). Together, these data demonstrate that VEGF increases both eNOS expression and activity in cultured endothelial cells.

Example 2

Negative Feedback of NO on eNOS Expression

The role of nitric oxide in VEGF-induced eNOS expression was investigated by co-incubation of VEGF with L-NAME (2 mM), an eNOS inhibitor, with SNAP, a nitric oxide donor, or with L-arginine, the substrate of eNOS. ACE cells were incubated with VEGF alone or in combination with an eNOS inhibitor, L-NAME. eNOS protein was detected by Western blot. The materials and methods used in this study were as described above for Example 1.

Figure 2:
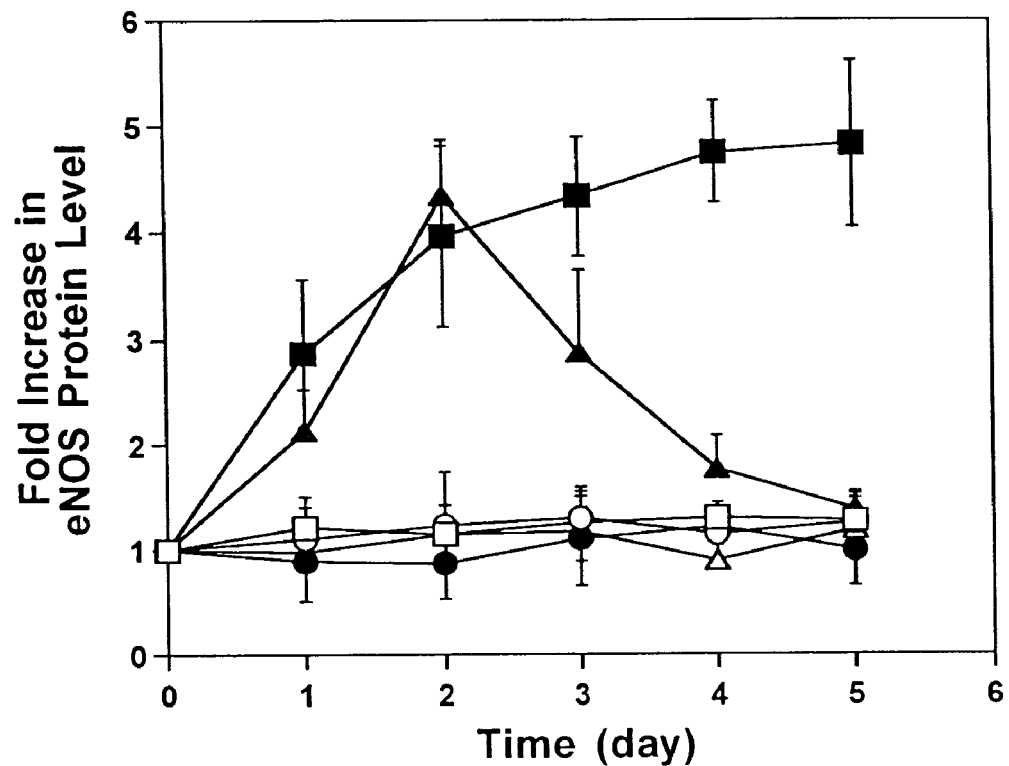
FIG. 2 is a graph showing the fold increase in eNOS protein following treatment with VEGF, L-NAME, SNAP (alone) or a combination of VEGF with L-NAME or SNAP for 0–5 days.

FIG. 2 shows that VEGF alone induced a time-dependent but transient increase in eNOS expression with a maximal effect at 2 days post-exposure. In contrast, co-incubation of L-NAME with VEGF resulted in a sustained increase in eNOS expression, whereas NO donor, SNAP, prevented both transient and sustained increase in eNOS (FIG. 2). These results suggest that nitric oxide produced by eNOS in endothelial cells in culture or from exogenous nitric oxide donors may have a negative feedback on eNOS expression.

Example 3

KDR Receptor Activation is Required for VEGF-induced eNOS Expression

Several approaches were used to determine which VEGF receptor was involved in VEGF-induced eNOS expression. First, VEGF receptor-selective variants which bind preferentially to either one of the VEGF receptors, KDR or FLT-1-, at equal concentrations, were incubated with ACE cells for two days. The specific agents used in this study and shown in FIG. 3A were: lane 1, control; lane 2, $VEGF_{165}$; lane 3, $VEGF_{110}$; lane 4, KDR-sel; lane 5, FLT-sel; lane 6, PLGF. eNOS protein was detected using the methods described for Example 1. The materials and methods used in this study were as described above for Example 1.

Figure 3A:
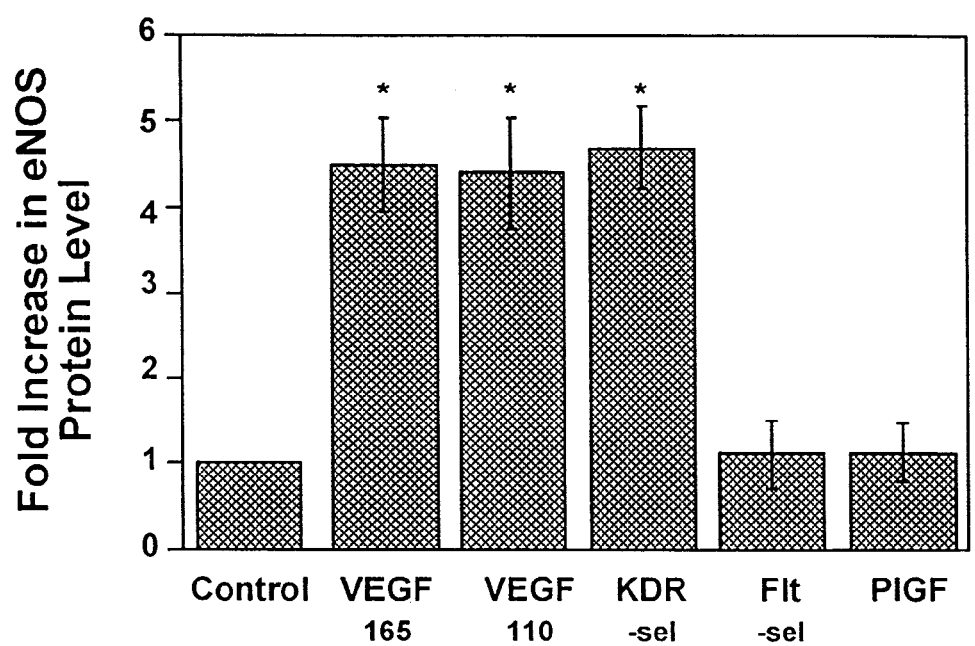
FIGS. 3A–3C depict the VEGF receptor specificities for eNOS regulation.

FIG. 3A shows that both $VEGF_{165}$ and $VEGF_{110}$, a heparin binding domain-deficient mutant with normal binding to KDR and FLT-1, induced a similar degree of eNOS expression. The KDR selective variant (KDR-sel) binds to KDR receptor normally but with reduced binding to FLT-1. The KDR-selective variant up-regulated eNOS expression, whereas the FLT-1 selective binding variant (FLT-sel) failed to do so. Placental growth factor (PLGF), which is known to only bind to FLT-1 receptor, had no effect on eNOS expression. These data suggest that the KDR receptor was the dominant receptor involved in VEGF-induced eNOS expression.

The involvement of KDR receptor in eNOS up-regulation was further confirmed by experiments in which receptor transfected porcine aorta endothelial (PAE) cells were used. PAE, PAE/KDR and PAE/Flt-1 cells were incubated with or without 500 pM rhVEGF for 2 days. eNOS was detected as described above for Example 1. Other materials and methods used in this study were as described above for Example 1.

Figure 3B:
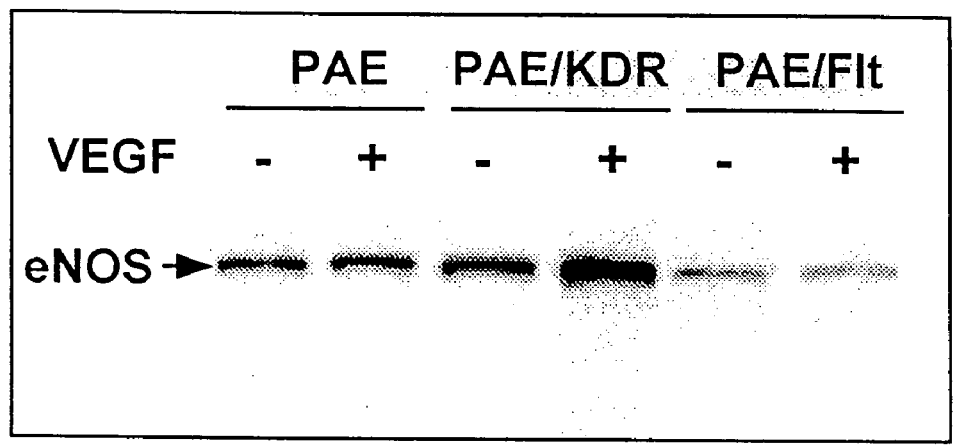

Data shown in FIG. 3B demonstrate that VEGF was able to induce eNOS up-regulation only in KDR-transfected PAE (PAE/KDR) cells, and not in FLT-1 transfected PAE (PAE/FLT) cells.

Figure 3C:
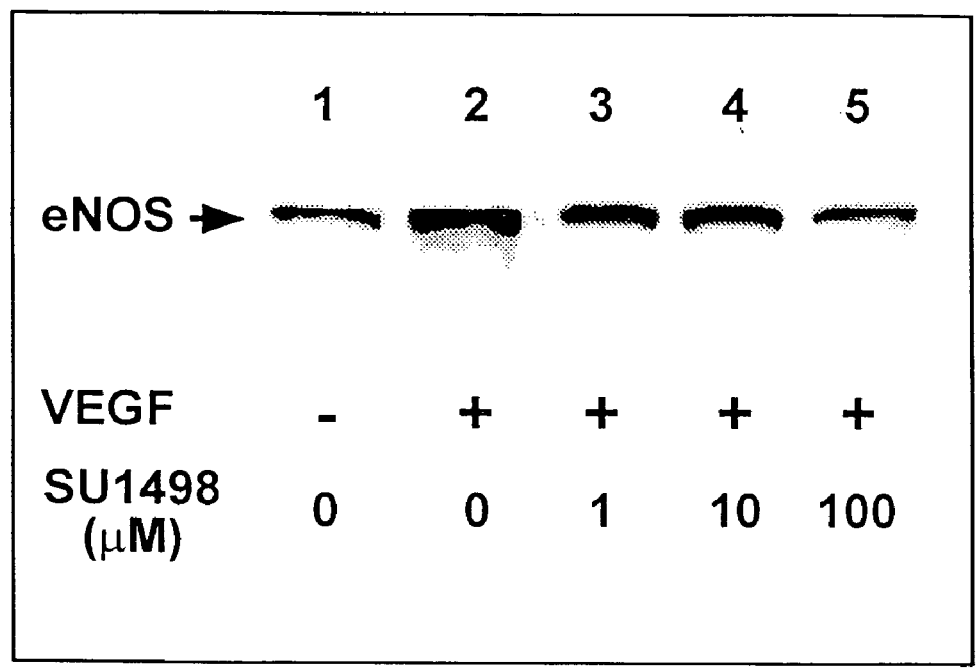

Activation of KDR receptor tyrosine kinase was shown to be required for eNOS up-regulation. Co-incubation of VEGF with a selective KDR tyrosine kinase inhibitor, SU-149 g caused a dose dependent inhibition of eNOS expression. (FIG. 3C)

The materials and methods used in this study were as described above for Example 1. Confluent ACE cells were co-incubated with SU1498 in combination with 500 pM rhVEGF for 2 days. The data shown is representative of 3 independent experiments.

At high concentration (100 µM), SU-1498 completely blocked VEGF-induced eNOS up-regulation. Taken together, these data demonstrate that KDR receptor activation is required for VEGF-induced eNOS expression.

Example 4

Inhibition of Tyrosine Kinase and/or PKC Inhibits VEGF-induced eNOS Expression

Various inhibitors were tested to investigate the role of down-stream signaling molecules following receptor activation in VEGF-induced eNOS expression. The materials and methods used in this study were as described above for Example 1. ACE cells were treated with specific tyrosine kinase inhibitors in combination with 500 pM rhVEGF for 2 days. eNOS protein was detected by Western blot.

Specific agents used and shown in FIG. 4 are: Lane 1, control (no VEGF or inhibitors); lane 2, VEGF (500 pM); lane 3, VEGF and herbimycin A ("Her"; 2 µM); lane 4, VEGF+PP1 (10 µM); lane 5, VEGF and staurosporin ("Sta"; 500 nM); lane 6, VEGF and GFX (GF109203X, 10 µM); lane 7, VEGF and Calphostin C ("Cal", 10 µM); lane 8, VEGF and chelerythrine chloride ("che", 10 µM); lane 9, VEGF and Go6976 ("Go", 10 µl M); lane 10, VEGF and Rotterlin Mallotoxin ("Rot", 50 µM); lane 11, VEGF and H8 (25 µM); lane 12, VEGF and H89 (25 µM). The data shown is representative of 3 independent experiments.

Figure 4A:
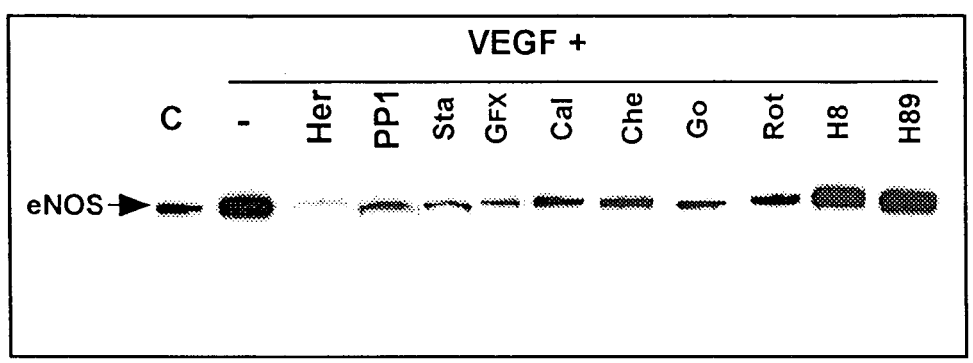
FIGS. 4A–4B depict the inhibition of VEGF modulation on eNOS.
Figure 4B:
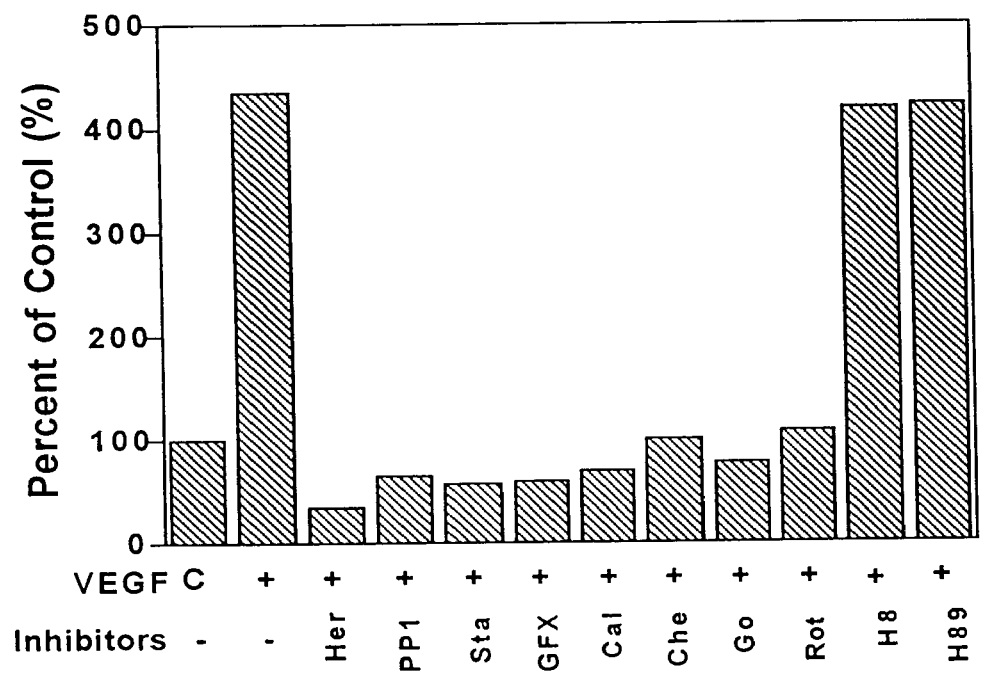

The data in FIG. 4A shows that inhibition of tyrosine kinase activity with genistein or herbimycin A, an irreversible and selective inhibitor of tyrosine kinase, blocked VEGF-induced eNOS expression. Furthermore, inhibition of PLC-gamma, the upstream signal molecule of PKC, with PP1 also blocked eNOS expression. Inhibition of P13-K with Wortmannin had no significant effect on eNOS expression. FIG. 4B shows the respective quantitation of eNOS levels using a densitometer.

Figure 5A:
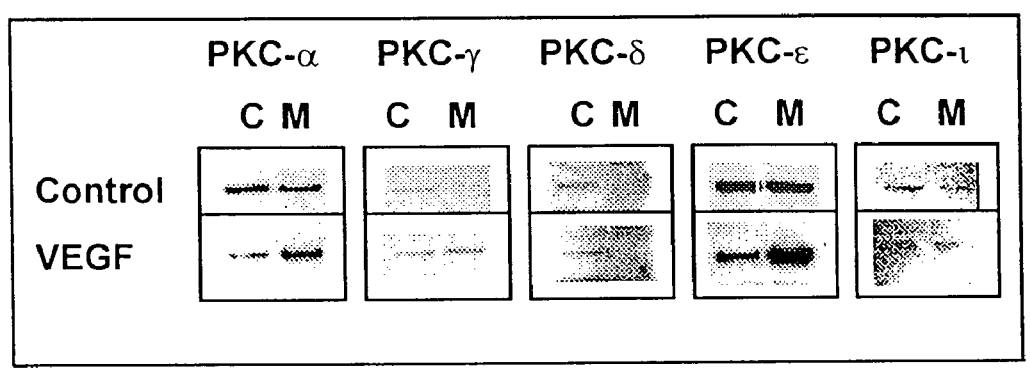
FIGS. 5A–5C depict PKC activity in eNOS modulation by VEGF.
Figure 5B:
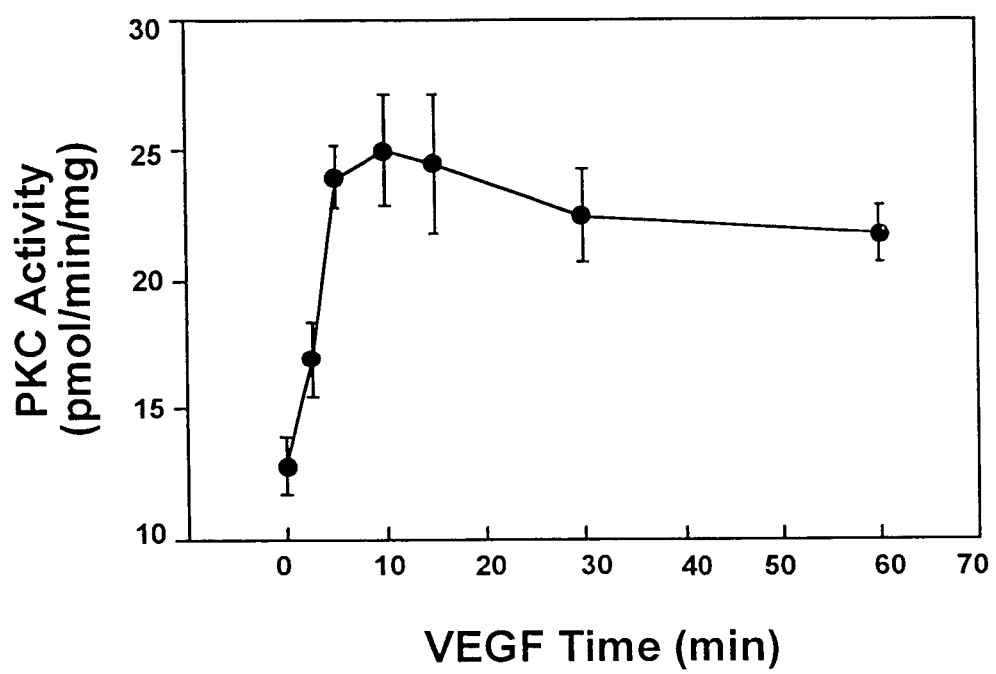

To examine the role of PKC isoforms and activation in VEGF-induced eNOS up-regulation, ACE cells were treated with rhVEGF (500 pM) for 10 minutes. Cytosolic and membrane fractions were prepared to investigate the redistribution or PKC isoforms. VEGF induced a rapid redistribution of PKC-alpha, -gamma, and -epsilon. (See FIG. 5A). In addition, VEGF treatment time-dependently increased PKC activity (FIG. 5B).

Figure 5C:

Incubation with PMA, a potent PKC activator, resulted in a time-dependent (FIG. 5C) and dose-dependent (data not shown) increase in eNOS levels. These data imply an important role for PKC activation and signaling in VEGF-induced eNOS expression.

Example 5

Effect of Other Angiogenic Factors on eNOS Expression

The effect of several other angiogenic factors including FGF, HGF, EGF, TGF-beta on eNOS expression was also studied. ACE cells were treated with equal molar concentrations (500 pM) of VEGF, HGF, FGF, EGF, TGF-beta1 or TGF-beta2 for 2 days. The materials and methods used in this study were as described above for Example 1.

Figure 6:
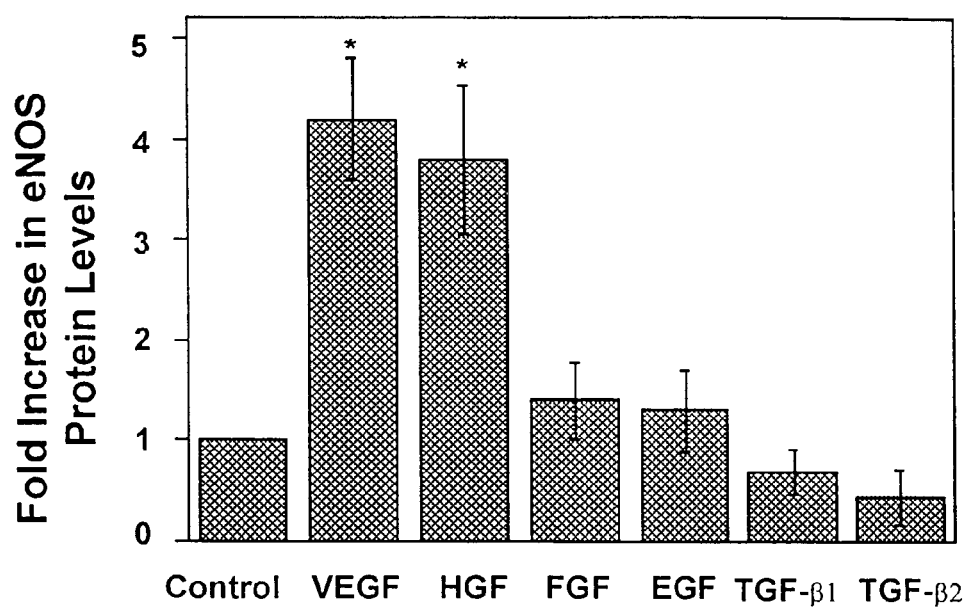
FIG. 6 is a bar diagram illustrating effects of various angiogenic factors on eNOS expression. The histograms show the fold increase in eNOS protein in growth factor treated cells normalized to untreated control cells.

FIG. 6 shows that in addition to VEGF, HGF is also capable of increasing eNOS expression, whereas FGF, EGF had no significant effect on eNOS expression. TGF-beta1 and TGF-beta2 reduced endogenous eNOS expression. These data indicate that VEGF and HGF are distinct from the other angiogenic growth factors in their ability to increase eNOS expression in vitro.

Example 6

Selection of KDR-Specific VEGF Variants

To generate KDR-specific variants, two phage libraries were constructed in which residues of VEGF(1–109) found to be important for Flt-1 binding but not KDR binding were randomly mutated.

Phagemid Construction

To construct the phage libraries, a phagemid vector having cDNA encoding residues 1–109 of VEGF was first produced. Phagemid vector pB2105 (Genentech, Inc.) was produced by PCR amplification of the cDNA encoding residues 1–109 of VEGF, using primers that allowed subsequent ligation of Nsi I/Xba I restriction fragment into the phagemid vector, phGHam-g3 (Genentech, Inc.). This introduced an amber codon immediately following residue 109 and fused the VEGF 1–109 cDNA to the C-terminal half of gIII encompassing residues 249 through 406.

In one library, all possible residue combinations were allowed for VEGF 1–109 at positions 18, 21, 22, and 25 (by using oligonucleotides that changed target codons to NNS sequences, where N=G, A, T or C, and S=C or G), and change was allowed at 40% probability for position 17 (by enforcing a 70% probability of wild-type and a 10% probability of each of the three other base types for each base in the target codon).

The following oligonucleotides were used to change target codons to NNS sequences:

L-528:    CAC GAA GTG GTG AAG <u>TTC</u> NNS GAT GTC
          NNS NNS CGC AGC NNS TGC CAT CCA ATC GAG
          (SEQ ID NO:1)

L-530: GGG GGC TGC TGC AAT NNS <u>GAG</u> NNS NNS GAG
       TGT GTG CCC ACT (SEQ ID NO:2).

In the second library, all possible residue combinations were allowed for VEGF 1–109 at positions 63, 65, and 66, and change was allowed at 40% probability for position 64.

Synthesis of Heteroduplex DNA

Heteroduplex DNA was synthesized according to a procedure adapted from Kunkel et al., *Meth. Enzym.* 204: 125–139 (1991). Through this method, a mutagenic oligonucleotide was incorporated into a biologically active, covalently closed circular DNA (CCC-DNA) molecule. The procedure was carried out according to the following steps.

First, the oligonucleotides described above were 5'-phosphorylated. This was done by combining in an eppendorf tube 2 µg oligonucleotide, 2 µl 10× TM buffer (500 mM Tris-HCl, 100 mM $MgCl_2$, pH 7.5), 2 µl 10 mM ATP, and 1 µl 100 mM DTT, and then adding water to a total volume of 20 µl. Twenty units of T4 polynucleotide kinase (Weiss units) were added to the mixture and incubated for 1 hour at 37° C.

Next, each 5'-phosphorylated oligonucleotide was annealed to a phagemid template (single-strand DNA purified from a dut-/ung- *E. coli* strain CJ-236). This was done by first combining 1 µg single strand DNA template, 0.12 µg phosphorylated oligonucleotide, and 2.5 µl 10× TM buffer (500 mM Tris-HCl, 100 mM $MgCl_2$, pH 7.5), adding water to a total volume of 25 µl. The DNA quantities provided an oligonucleotide to template molar ratio of 3:1, assuming that the oligonucleotide to template length ratio is 1:100. The mixture was incubated at 90° C. for 2 minutes, then incubated at 50° C. for 3 minutes, and then incubated at 20° C. for 5 minutes.

Each 5'-phosphorylated oligonucleotide was then enzymatically extended and ligated to form a CCC-DNA molecule by adding the following reagents to the annealed mixture: 1 µl 10 mM ATP, 1 µl 25 mM dNTPs, 1.5 µl 100 mM DTT, 3 units T4 DNA ligase, and 3 units T7 DNA polymerase. The mixture was then incubated at 20° C. for at least 3 hours.

The DNA was purified by ethanol precipitation and resuspended in 15 µl of water.

*E. coli* Electroporation

The library phage were produced in a supressor strain of *E. coli* known as *E. coli* XL1-blue (Stratagene, LaJolla, Calif.) by *E. coli* electroporation. For electroporation, purified heteroduplex DNA first was chilled in a 0.2-cm gap electroporation cuvet on ice, and a 100 µl aliquot of electrocompetent *E. coli* XL1-blue was thawed on ice. The *E. coli* cells were added to the DNA and mixed by pipetting several times.

The mixture was transferred to the cuvet and electroporated using a Gene Pulser (Bio-rad, Hercules, Calif.) with the following settings: 2.5 kV field strength, 200 ohms resistance, and 25 mF capacitance. Immediately thereafter, 1 ml of SOC media (5 g bacto-yeast extract, 20 g bacto-tryptone, 0.5 g NaCl, 0.2 g KCl; add water to 1 liter and adjust pH to 7.0 with NAOH; autoclave; then add 5 mL of autoclaved 2 M $MgCl_2$ and 20 mL of filter sterilized 1 M glucose) was added and the mixture was transferred to a sterile culture tube and grown for 30 minutes at 37° C. with shaking.

To determine the library diversity, serial dilutions were plated on 2YT (10 g bacto-yeast extract, 16 g bacto-tryptone, 5 g NaCl; add water to] liter and adjust pH to 7.0 with NAOH; autoclave) plates (supplemented with 50 µg/ml ampicillin). Additionally, the culture was transferred to a 250-ml baffled flask containing 25 ml 2YT, 25 mg/ml ampicillin, M13-VCS ($10^{10}$ pfu/mL) (Stratagene, LaJolla, Calif.), and incubated overnight at 37° C. with shaking.

The culture was then centrifuged for 10 minutes at 10 krpm, 2° C., in a Sorvall GSA rotor (16000 g). The supernatant was transferred to a fresh tube and ⅕ volume of PEG-NaCl solution (200 g/L PEG-8000, 146 g/L NaCl; autoclaved) was added to precipitate the phage. The supernatant/PEG-NaCl solution was incubated for 5 minutes at room temperature and centrifuged again to obtain a phage pellet.

The supernatant was decanted and discarded. The phage pellet was recentrifuged briefly and the remaining supernatant was removed and discarded. The phage pellet was resuspended in 1/20 volume of PBT buffer (PBS, 0.2% BSA, 0.1% Tween 20), and insoluble matter was removed and discarded by centrifuging the resuspended pellet for 5 minutes at 15 krpm, 2° C., in a SS-34 rotor (27000 g). The remaining supernatant contained the phage.

The supernatant was saved and used for sorting VEGF variants by their binding affinities. By producing the phage in a suppressor strain of *E. coli*, VEGF (1–109) variants-gIII fusion protein were expressed and displayed on the phage surface, allowing the phage to bind to KDR and/or Flt-1 receptors.

Affinity Sorting of the Libraries

Each library was sorted for binding to KDR (1–3) monomer using a competitive binding technique similar to a method used by H. Jin, *J. Clin. Invest.*, 98: 969 (1996), and shown to be useful for generating receptor-selective variants.

To conduct the competitive binding technique, each library was sorted for binding to immobilized KDR (1–3) monomer (Genentech, South San Francisco, Calif.) in the presence of a high concentration (100 nM) of competing Flt-1 (1–3) monomer (Genentech, Inc.) in solution. This was accomplished by first coating Maxisorp immunoplate wells (Nalge Nunc International, Rochester, N.Y.) with 80 µl per well of 2–5 µg/ml of KDR (1–3) monomer in coating buffer (50 mM sodium carbonate at pH 9.6) and incubating overnight at 4° C. The number of wells required depends on the diversity of the library. The coating solution was removed and blocked for 1 hour with 200 µl of 0.2% BSA in PBS. At the same time, an equal number of uncoated wells were blocked as a negative control.

The wells were washed eight times with PT buffer (PBS, 0.05% Tween 20) to remove the block buffer. Aliquots of 100 µl of library phage solution ($10^{12}$ phage/ml) in PBT buffer (PBS, 0.2% BSA, 0.1% Tween 20) were then added to each of the coated and uncoated wells. The Flt-1 (1–3) monomer was added with the phage solution. The wells were incubated at room temperature for 2 hours with gentle shaking.

The wells were then washed 10 times with PT buffer (PBS, 0.05% Tween 20) to remove the phage solution and any Flt-1-bound phage. KDR-bound phage was eluted from the wells by incubating the wells with 100 µl of 0.2 mM glycine at pH 2 for 5 minutes at room temperature. To collect the KDR-bound phage, the glycine solution was transferred to an eppendorf tube and neutralized with 1.0 M Tris-HCl at pH 8.0.

The KDR-bound phage were then repropagated by adding half of the eluted phage solution to 10 volumes of actively growing *E. coli* XL1-blue ($OD_{600}$<10) and incubating for 30 minutes at 37° C. with shaking. The serial dilutions of the culture were then plated on 2YT/amp plates (2YT being supplemented with 50 mg/ml ampicillin) to determine the number of phage eluted. This was determined for both the wells coated with KDR (1–3) monomer and the uncoated control wells.

The culture from the plates was transferred to 10 volumes of 2YT/amp/VCS (2 YT being supplemented with 50 mg/ml ampicillin and 10$^{10}$ pfu/ml M13-VCS) and incubated overnight at 37° C. with shaking. The phage were then isolated.

The phage that were repropagated were again sorted for binding to immobilized KDR (1–3) monomer in the presence of a high concentration (100 nM) of competing Flt-1 (1–3) monomer, followed by washing away the Flt-1-bound phage and repropagating the KDR-bound phage. The affinity sort procedure was monitored by calculating the enrichment ratio and was repeated until the enrichment ratio reached a maximum (about 5 to 6 sorting cycles).

The enrichment ratio is the number of phage eluted from a well coated with KDR (1–3) monomer divided by the number of phage binding to an uncoated control well. A ratio greater than one is usually indicative of phage binding specifically to the KDR (1–3) protein, thereby indicating resistance to binding to added Flt-1 (1–3) monomer. When the enrichment ratio reached a maximum, individual clones were analyzed for specific binding.

Phage ELISA

Specific binding of phage having VEGF 1–109 variant-gIII protein on its surface to the KDR (1–3) monomer was measured using a phage ELISA according to Muller et al., *PNAS*, 94: 7192 (1997). For the phage ELISA, microtiter plates (Maxisorp, Nunc-Immunoplate, Nalge Nunc International, Rochester, N.Y.) were coated with purified KDR (1–3) monomer or Flt-1 (1–3) monomer (5ug/ml) in 50 mM sodium carbonate at pH 9.6 and incubated at 4° C. overnight. The plates were blocked with 0.5% BSA. Next, serial dilutions of VEGF 1–109 variants together with a subsaturating concentrating of competing receptor (KDR (1–3) monomer or Flt-1 (1–3) monomer) were added to wells in 100 ul of binding buffer (PBS, 0.5% Tween20, 0.5% BSA). After equilibrium, the plates were washed, and the bound phagemid were stained with horseradish peroxidase-conjugated anti-M13 antibody (Pharmacia Biotech, Piscataway, N.J.), following manufacturer instructions. Affinities (EC50) were calculated as the concentration of competing receptor that resulted in half-maximal phagemid binding.

The sequences of VEGF 1–109 variants which were obtained from the affinity sorting and which showed resistance to Flt-1 (1–3) monomer were determined from the sequence of the phagemid cDNA.

Purification of VEGF 1–109 Variants

VEGF 1–109 variant proteins were isolated as retractile bodies from the shake flask culture of *E. coli* (27c7). The refolding of the mutant proteins was performed as described by Yihai et al., *J. Biol. Chem.,* 271: 3154–3162 (1996). The variants were mixed and unfolded with 6 M guanidine HCL plus 1 mM oxidized glutathione at pH 6, and dialyzed against 10 volumes of 2 M urea with 2 mM reduced glutathione and 0.5 mM of oxidized glutathione in 20 mM Tris-HCL at pH 8 for 10 hours. Urea was removed by dialyzing slowly against 20 volumes of 20 mM Tris-HCL (pH 8) overnight at 4° C. Each of the variants was purified further by anion exchange (Pharmacia HiTrap Q, 1 ml) (Pharmacia Biotech, Piscataway, N.J.), to remove traces of misfolded monomer. The identity of the resulting pure variants was confirmed by SDS-PAGE and mass spectrometry.

Table 2 shows the VEGF variant identifier name, the amino acid substitutions introduced, and the codon encoding the respective substituted amino acids. The asterisk (*) next to certain variant identifiers (such as LK-VRB-1s) indicates various VEGF variants which demonstrated particularly preferred binding affinities and/or biological activities. The variant identifiers which contain an "s" (such as LK-VRB-1s) indicate VEGF variant polypeptides which consisted of the 1–109 truncated form of VEGF and contained the recited mutations provided in the Table. The variant identifiers which contain an "f" (such as LK-VRB-1f) indicate VEGF variant polypeptides which consisted of the full length 1–165 form of VEGF (amino residues 27–191 of SEQ ID NO: 4) and contained the recited mutations provided in the Table. The VEGF $_{165}$ was encoded by the nucleotide sequence of SEQ ID NO: 3. The naming and identification of the mutations in the variant sequences is in accord with naming convention. For example, for the first entry in Table 2, the mutation is referred to as "M18E". This means that the 18 position of the native VEGF sequence (using the numbering in the amino acid sequence for native human VEGF as reported in Leung et at, supra and Houck et al, supra) was mutated so that the native methionine (M) at that position was substituted with a glutamic acid (E) residue to prepare the VEGF variant. The column in Table 2 referred to as "Nucleotide Sequence" provides the respective codons coding (5'→3') for each of the respective amino acid mutations. For example, for the first entry in Table 2, the M18E mutation is coded by the codon "GAG."

TABLE 2

VEGF Variants and Corresponding Mutations

| Variant Identifier | Amino Acid Mutation | Nucleotide Sequence |
|---|---|---|
| LK-VRB-1s* | M18E/Y21L/Q22R/Y25S | GAG/CTC/CGG/AGC |
| LK-VRB-2s* | D63S/G65M/L66R | AGC/ATG/CGC |
| LK-VRB-3s | F17I/M18E/Y21F/Q22K/Y25S | ATT/CAG/TTC/AAG/AGC |
| LK-VRB-4s | F17I/M18E/Y21F/Q22E/Y25I | ATC/GAG/TTC/GAG/CAC |
| LK-VRB-5s | D63S/L66R | AAG/CAG |
| LK-VRB-6s | D63S/G65A/L66T | AAG/GGC/ATG |
| LK-VRB-7s* | M18E/D63S/G65M/L66R | GAG/AGC/ATG/CGC |
| LK-VRB-8s* | Y2IL/D63S/G65M/LG6R | CTC/AGC/ATG/CGC |
| LK-VRB-9s | Q22R/D63S/G65M/L66R | CGG/AGC/ATG/CGC |
| LK-VRB-10s | Y25S/D63S/G65M/L66R | AGC/AGC/ATG/CGC |
| LK-VRB-11s | M18E/Y21L/D63S/G65M/L66R | GAG/CTC/AGC/ATG/CGC |
| LK-VRB-12s | M18E/Q22R/D63S/G65M/L66R | GAG/CGG/AGC/ATG/CGC |
| LK-VRB-13s | M18E/Y25S/D63S/G65M/L66R | GAG/AGC/AGC/ATG/CGC |
| LK-VRB-14s | Y21L/Q22R/D63S/G65M/L66R | CTC/CGG/AGC/ATG/CGC |
| LK-VRB-15s | Y21L/Y25S/D63S/G65M/L66R | CTC/AGC/AGC/ATG/CGC |
| LK-VRB-16s | Q22R/Y25S/D63S/G65M/L66R | CGG/AGC/AGC/ATG/CGC |
| LK-VRB-17s | M18E/Y21L/Q22R/D63S/G65M/L66R | GAG/CTC/GAG/AGC/ATG/CGC |
| LK-VRB-18s | M18E/Q22R/Y25S/D63S/G65M/L66R | GAG/CGG/AGC/AGC/ATG/CGC |
| LK-VRB-19s | M18E/Q22R/Y25S/D63S/G65M/L66R | GAG/CGG/AGC/AGC/ATG/CGC |
| LK-VRB-20s | Y21L/Q22R/Y25S/D63S/G65M/L66R | CTC/CGG/AGC/AGC/ATG/CGC |
| LK-VRB-21s | D63S/M18E/Y21L/Q22R/Y25S | TCC/GAG/CTC/CGG/AGC |
| LK-VRB-22s | GG5M/M18E/Y21L/Q22R/Y25S | ATG/GAG/CTC/CGG/AGC |
| LK-VRB-23s | L66R/M185/Y21L/Q22R/Y25S | AGG/GAG/CTC/CGG/AGC |
| LK-VRB-24s | D63S/G65M/M18E/Y21L/Q22R/Y25S | TCC/ATG/GAG/CTC/CGG/AGC |

TABLE 2-continued

VEGF Variants and Corresponding Mutations

| Variant Identifier | Amino Acid Mutation | Nucleotide Sequence |
|---|---|---|
| LK-VRB-25s | D63S/L66R/ M18E/Y21L/Q22R/Y25S | TCC/AGG/ GAG/CTC/CGG/AGC |
| LK-VRB-26s | G65M/L66R/ M18E/Y21L/Q22R/Y25S | ATG/AGG/ GAG/CTC/CGG/AGC |
| LK-VRB-27s | M18E/Y21L/Q22R/Y25S/D63S/ G65M/L66R | GAG/CTC/CGG/ AGC/AGC/ATG/CGC |
| LK-VRB-1f | M18E/Y21L/Q22R/Y25S | GAG/CTC/CGG/AGC |
| LK-VRB-2f | D63S/G65M/L66R | AGC/ATG/CGC |

Example 7

Binding of VEGF Variants to KDR Receptor

The binding of VEGF (1–109) variants and VEGF165 variants (described in Example 6) to KDR receptor was evaluated by measuring the ability of the variants to inhibit binding of biotinylated native VEGF (8–109) to KDR receptor. The VEGF variants evaluated contained the mutations shown in Table 2.

Receptor binding assays were performed in 96-well immunoplates (Maxisorp, Nunc-Immunoplate, Nalge Nunc International, Rochester, N.Y.). Each well was coated with 100 µl of a solution containing 8 µg/ml of a monoclonal antibody to KDR known as MAKD5 (Genentech, South San Francisco, Calif.) in 50 mM carbonate buffer at pH 9.6 and incubated at 4° C. overnight. The supernatant was discarded, the wells were washed three times in washing buffer (0.05% Tween 20 in PBS), and the plate was blocked (150 µl per well) with block buffer (0.5% BSA, 0.01% thimerosal in PBS) at room temperature for one hour. The supernatant was discarded, and the wells were washed.

Serially diluted native VEGF(8–109), native VEGF (1–165), native VEGF (1–109) variants, or VEGF165 variants (0.16–168 nM in monomer) were incubated with biotinylated native VEGF (8–109) (84 nM) and KDR (1–3) (1 µg/ml) for 2 hours at room temperature in assay buffer (0.5% BSA, 0.05% Tween 20 in PBS). Aliquots of this mixture (100 µl) were added to the precoated microtiter wells and the plate was incubated for 1 hour at room temperature. The complex of KDR (1–3) and biotinylated native VEGF that was bound to the microtiter plate was detected by incubating the wells with peroxidase-labeled streptavidin (0.2 mg/ml, Sigma, St. Louis, Mo.) for 30 minutes at room temperature. The wells were then incubated with 3, 3', 5,5'-tetramethyl benzidine (0.2 gram/liter; Kirkegaard & Perry Laboratories, Gaithersburg, Md.) for about 10 minutes at room temperature. Absorbance was read at 450 nm on a Vmax plate reader (Molecular Devices, Menlo Park, Calif.).

Figure 7:
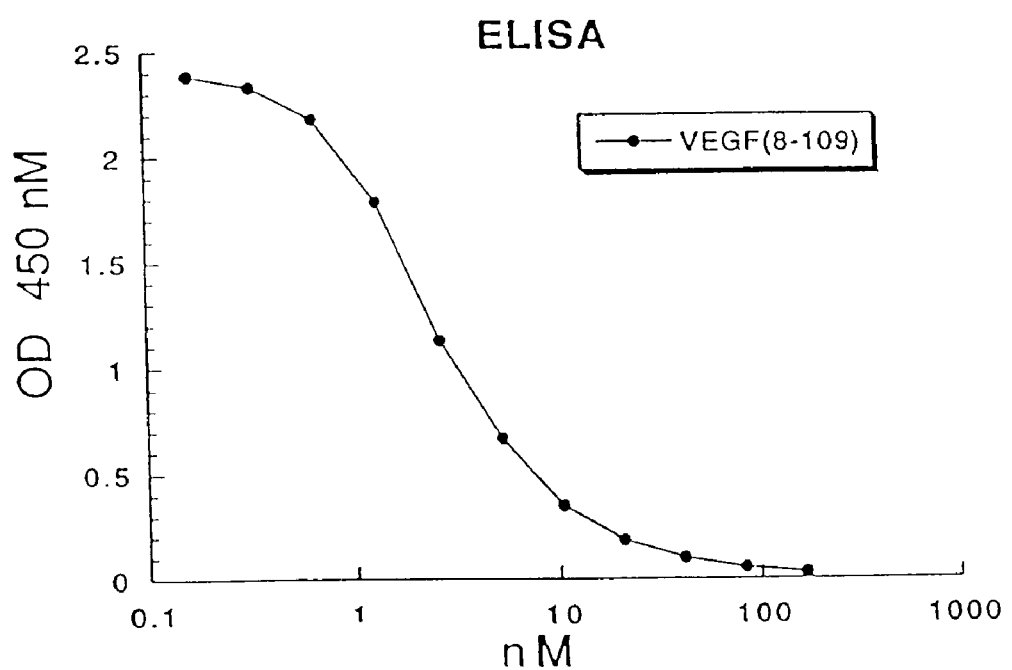
FIG. 7 depicts the ELISA assay titration curve for the native VEGF (8–109).

Titration curves were fit with a four-parameter nonlinear regression curve-fitting program (KaleidaGraph, Synergy Software, Reading, Pa.). Concentrations of VEGF variants corresponding to the midpoint absorbance of the titration curve of the native VEGF (8–109) were calculated and then divided by the concentration of the native VEGF corresponding to the midpoint absorbance of the native VEGF titration curve. (See FIG. 7)

The binding affinities determined for the VEGF (1–109) variants and VEGF165 variants are shown in Table 3. Many of the VEGF variants exhibited binding to KDR receptor that was within about two-fold of the binding of native VEGF (8–109).

Example 8

Binding of VEGF Variants to Flt-1 Receptor

The binding of the VEGF (1–109) variants and VEGF165 variants (described in Example 6) to Flt-1 receptor was evaluated by measuring the ability of the variants to inhibit binding of biotinylated native VEGF (8–109) to Flt-1 receptor. The VEGF variants evaluated contained the mutations shown in Table 2.

Receptor binding assays were performed in 96-well immunoplates (Maxisorp, Nunc-Immunoplate, Nalge Nunc International, Rochester, N.Y.). Each well was coated with 100 µl of a solution containing 2 µg/ml of rabbit F(ab')2 to human IgG Fc (Jackson ImmunoResearch, West Grove, Pa.) in 50 mM carbonate buffer at pH 9.6 and incubated at 4° C. overnight. The supernatant was then discarded, the wells were washed three times in washing buffer (0.05% Tween 20 in PBS), and the plate was blocked (150 µl per well) with block buffer (0.5% BSA, 0.01% thimerosal in PBS) at room temperature for one hour. The supernatant was discarded, and the wells were washed.

The wells were filled with 100 µl of a solution containing Flt-IgG (a chimeric Flt-human Fc molecule) at 50 ng/ml in assay buffer (0.5% BSA, 0.05% Tween 20 in PBS). The wells were incubated at room temperature for 1 hour and then washed three times in wash buffer (0.05% Tween 20 in PBS).

Serially diluted native VEGF(8–109), native VEGF165, VEGF (1–109) variants, or VEGF165 variants (0.03–33 nM in monomer) were mixed with biotinylated native VEGF (8–109) (0.21 nM) or biotinylated native VEGF165 (0.66 nM). Aliquots of the mixture (100 µl) were added to the precoated microtiter wells and the plate was incubated for 2 hours at room temperature. The complex of Flt-IgG and biotinylated native VEGF that was bound to the microtiter plate was detected by incubating the wells with peroxidase-labeled streptavidin (0.2 mg/ml, Sigma, St. Louis, Mo.) for 30 minutes at room temperature. The wells were then incubated with 3, 3', 5,5'-tetramethyl benzidine (0.2 g/liter, Kirkegaard & Perry Laboratories, Gaithersburg, Md.) for about 10 minutes at room temperature. Absorbance was read at 450 nm on a Vmax plate reader (Molecular Devices, Menlo Park, Calif.).

Titration curves were fit with a four-parameter nonlinear regression curve-fitting program (KaleidaGraph, Synergy Software, Reading, Pa.). Concentrations of VEGF variants corresponding to the midpoint absorbance of the titration curve of the native VEGF (8–109) were calculated and then divided by the concentration of the native VEGF corresponding to the midpoint absorbance of the native VEGF titration curve.

The binding affinities determined for the VEGF (1–109) variants and VEGF165 variants are shown in Table 3. Many of the VEGF variants exhibited binding to Flt-1 receptor that was more than 2,000-fold less than the binding of native VEGF (8–109). The relative binding affinity data reported in Table 3 for certain VEGF variants (for instance, LK-VRB-7s* and LK-VRB-8s*) to FLT-1 receptor is not reported in nM values since the amount of detectable binding was beyond the sensitivity of the ELISA assay.

TABLE 3

Binding of VEGF Variants to KDR Receptor and FLT-1 Receptor

| Variant Identifier | Relative Binding Affinity | |
| --- | --- | --- |
| | KDR Receptor | FLT-1 Receptor |
| LK-VRB-1s* | 1 nM/1 | 2700 nM/6000 |
| LK-VRB-2s* | 1 nM/1 | >400 nM/>1000 |
| LK-VRB-3s | 1 nM/1 | 170 nM/400 |
| LK-VRB-4s | 1 nM/1 | 100 nM/200 |
| LK-VRB-5s | 1 nM/1 | 233 nM/550 |
| LK-VRB-6s | 0.5 nM/0.5 | 4 nM/10 |
| LK-VRB-7s* | 1 nM/1 | />15000 |
| LK-VRB-8s* | 0.5 nM/0.5 | />21000 |
| LK-VRB-9s | 0.5 nM/0.5 | />300 |
| LK-VRB-10s | 0.5 nM/0.5 | />2400 |
| LK-VRB-11s | 2 nM/2 | />14000 |
| LK-VRB-12s | 0.4 nM/0.4 | />5600 |
| LK-VRB-13s | 14 nM/14 | />14000 |
| LK-VRB-14s | 0.5 nM/0.5 | />2900 |
| LK-VRB-15s | 2 nM/2 | />21000 |
| LK-VRB-16s | 0.6 nM/0.6 | />1400 |
| LK-VRB-17s | 3 nM/3 | />1900 |
| LK-VRB-18s | 130 nM/130 | />3900 |
| LK-VRB-19s | 7 nM/7 | />35000 |
| LK-VRB-20s | 2 nM/2 | />10000 |
| LK-VRB-21s | 3 nM/3 | />5600 |
| LK-VRB-22s | 4 nM/4 | />30 |
| LK-VRB-23s | 11 nM/11 | />8500 |
| LK-VRB-24s | 10 nM/10 | />18000 |
| LK-VRB-25s | 4 nM/4 | />12000 |
| LK-VRB-26s | 23 nM/23 | />25000 |
| LK-VRB-2f | 1 nM/1 | 19 nM/70 |
| Compare Native VEGF (8-109) | 1 nM/1 | 0.42 nM/1 |

Example 9

Induction of KDR Receptor Phosphorylation by VEGF (1–109) Variants

To determine the activity of the VEGF variants, the ability of the variants to induce phosphorylation of the KDR receptor was measured in a KIRA assay. The VEGF variants evaluated contained the mutations found in Table 2. Specifically, the following VEGF (1–109) variants were studied: LK-VRB-1s*; LK-VRB-2s*; LK-VRB-3s; LK-VRB-4s; LK-VRB-5s; and LK-VRB-6s.

Serially diluted VEGF (1–109) variants (0.01–10 nM) were added to CHO cells that express the KDR receptor with a gD tag at the N-terminus (Genentech, South San Francisco, Calif.). Cells were lysed by 0.5% Triton-X100, 150 mM NaCl, 50 mM Hepes at pH 7.2, and phosphorylated gD-KDR receptor in the lysate was quantified by conducting an ELISA.

For the ELISA, 96-well immunoplates (Maxisorp, Nunc-Immunoplate, Nalge Nunc International, Rochester, N.Y.) were used. Each well was coated with 100 μl of a solution containing 1 μg/ml of a mouse monoclonal antibody to gD known as 3C8 (Genentech, South San Francisco, Calif.) in 50 mM carbonate buffer at pH 9.6 and incubated overnight at 4° C. The supernatant was discarded, the wells were washed three times in washing buffer (0.05% Tween 20 in PBS), and the plate was blocked (150 μl per well) in block buffer (0.5% BSA, 0.01% thimerosal in PBS) for 1 hour at room temperature. The supernatant was then discarded, and the wells were washed.

Aliquots of the lysate (100 μl) were added to the precoated wells and incubated for 2 hours at room temperature. The phosphorylated gD-KDR receptor was detected by incubating the wells with biotinylated monoclonal antibody to phosphotyrosine known as 4G10 (0.05 mg/ml) (Upstate Biotechnology, Lake Placid, N.Y.) for 2 hours at room temperature followed by incubating the wells with peroxidase-labeled streptavidin (0.2 mg/ml, Sigma, St. Louis, Mo.) for 1 hour at room temperature. The wells were then incubated with 3, 3', 5,5'-tetramethyl benzidine (0.2 g/liter, Kirkegaard & Perry Laboratories, Gaithersburg, Md.) for about 15–20 minutes at room temperature. Absorbance was read at 450 nm on a Vmax plate reader (Molecular Devices, Menlo Park, Calif.).

Figure 8:
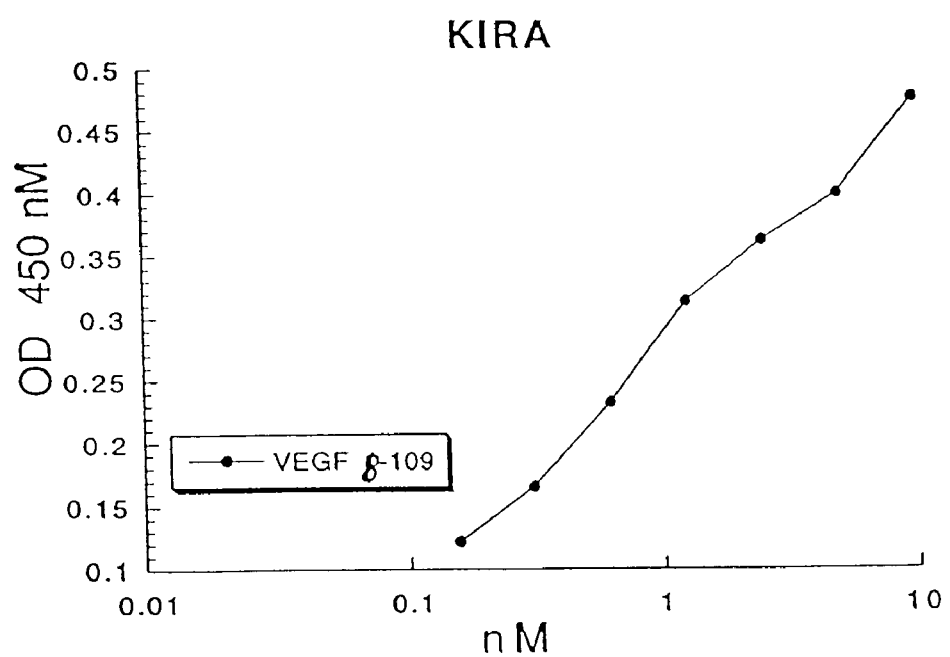
FIG. 8 depicts the KIRA assay titration curve for the native VEGF (8–109).

Titration curves were fit with a four-parameter nonlinear regression curve-fitting program (KaleidaGraph, Synergy Software, Reading, Pa.). Concentrations of VEGF variants corresponding to the midpoint absorbance of the titration curve of the native VEGF (8–109) were calculated and then divided by the concentration of the native VEGF corresponding to the midpoint absorbance of the native VEGF titration curve. (FIG. 8)

The phosphorylation-inducing activity of the VEGF variants are provided in Table 4. The VEGF variants generally exhibited phosphorylation-inducing activity that was within two-fold of the activity of native VEGF (8–109).

TABLE 4

Induction of KDR Receptor Phosphorylation By VEGF (1-109) Variants

| Variant Identifier | Phosphorylation-Inducing Activity |
| --- | --- |
| LK-VRB-1s* | 1 nM/0.5 |
| LK-VRB-2s* | 2 nM/1 |
| LK-VRB-3s | 2 nM/1 |
| LK-VRB-4s | 1 nM/0.5 |
| LK-VRB-5s | 1 nM/0.5 |
| LK-VRB- 6s | 1 nM/0.5 |
| Compare Native VEGF (8-109) | 2 nM/1 |

Example 10

Endothelial Cell Proliferation Assay

The mitogenic activity of VEGF (1–109) or VEGF165 variants (as well as one VEGF165 variant, LK-VRB-2f) was determined by using human umbilical vein endothelial cells (HUVEC) (Cell Systems, Kirkland, Wash.) as target cells. The VEGF variants evaluated contained the mutations in Table 2. Specifically, the following VEGF (1–109) variants were studied: LK-VRB-1s*; LK-VRB-2s*; LK-VRB-7s*; and LK-VRB-8s*.

HUVEC is a primary cell line that is maintained and grown with growth factors such as acidic FGF in CS-C Complete Growth media (Cell Systems, Kirkland, Wash.). To prepare for the assay, an early passage (less than five passages) of the cells was washed and seeded in 96-well plates (3000 cells in 100 μl per well) and fasted in CS—C media without any growth factors but supplemented with 2% Diafiltered Fetal Bovine Serum (GibcoBRL, Gaithersburg, Md.) for 24 hours at 37° C. with 5% $CO_2$ incubator before replacing with fresh fasting media. VEGF variants at several concentrations (about 10 nM to 0.01 nM) diluted in the same fasting media were added to the wells to bring the volume to 150 μl per well and incubated for 18 hours.

To measure the DNA synthesis induced by the VEGF variants, $^3$H-thymidine (Amersham Life Science, Arlington Heights, Ill.) was added to each well at 0.5 μCi per well and incubated for another 24 hours for the cells to take up the radioactivity. The cells were then harvested onto another 96-well filter plate and the excess label was washed off before loading the plates on the Topcount (Packard, Meriden, Conn.).

Figure 9:
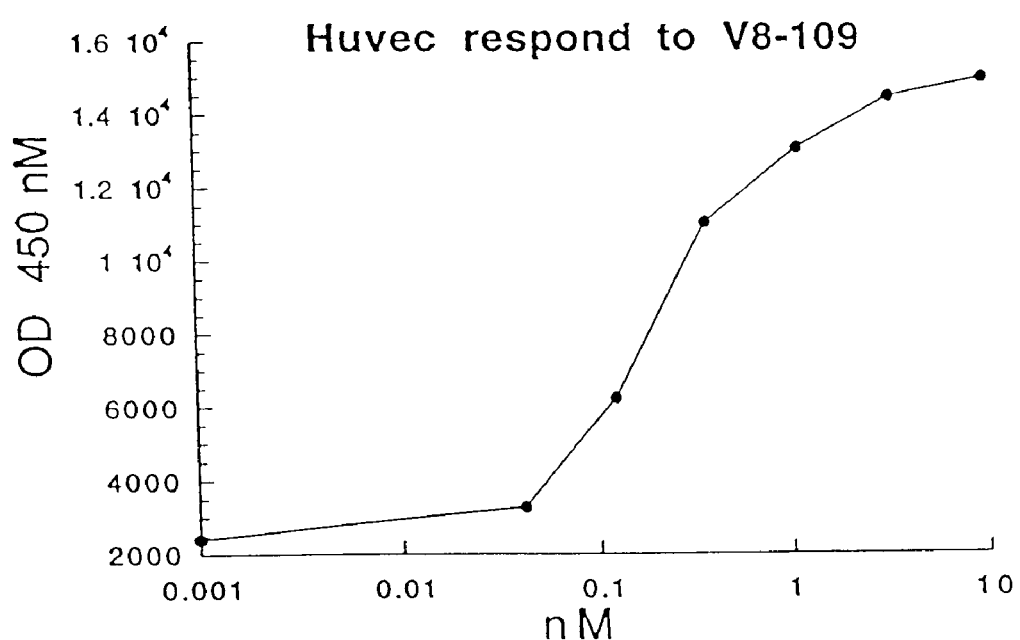
FIG. 9 depicts the HUVEC proliferation assay titration curve for the native VEGF (8–109).

The cells were counted by Topcount. The measured counts per minute (CPM) were plotted against the concentration of individual variants to compare their activities. (FIG. 9)

The cell proliferation capabilities of the VEGF variants are shown in Table 5. The VEGF variants generally exhibited cell proliferation capability that was within two-fold of the capability of native VEGF (8–109).

TABLE 5

Mitogenic Activity of VEGF (1-109) Variants

| Variant Identifier | Endothelial Cell Proliferation Activity |
| --- | --- |
| LK-VRB-1s* | 0.1 nM/0.2 |
| LK-VRB-2s* | 0.05 nM/0.1 |
| LK-VRB-7s* | 0.5 nM/1 |
| LK-VRB-8s* | 0.5 nM/1 |
| LK-VRB-2f | 0.05 nM/0.1 |
| Compare Native VEGF (8-109) | 0.5 nM/1 |

Example 11

RIA Assay to Determine Binding of VEGF Variants to KDR and FLT-1 Receptors

An RIA assay was conducted essentially as described in Muller et al., *PNAS*, 94:7192–7197 (1997) to examine relative binding affinities of several of the VEGF variants (described in Table 2) to the KDR receptor and FLT-1 receptor, as compared to native VEGF 165 or native VEGF (8–109). The results are shown below in Table 6.

TABLE 6

| | Relative Binding Affinity | |
| --- | --- | --- |
| Variant Identifier | KDR Receptor | FLT-1 Receptor |
| Native VEGF 165 | 1 (97 pM) | 1 (37 pM) |
| Native VEGF (8-109) | 12 | 29 |
| LK-VRB-1f | 8 | 1700 |
| LK-VRB-1s* | 20 | 14,000 |
| LK-VRB-2f | 1 | 2400 |
| LK-VRB-2s* | 2 | 27,000 |

Example 12

Up-Regulation of eNOS by KDR-Specific VEGF Variants

Figure 10:
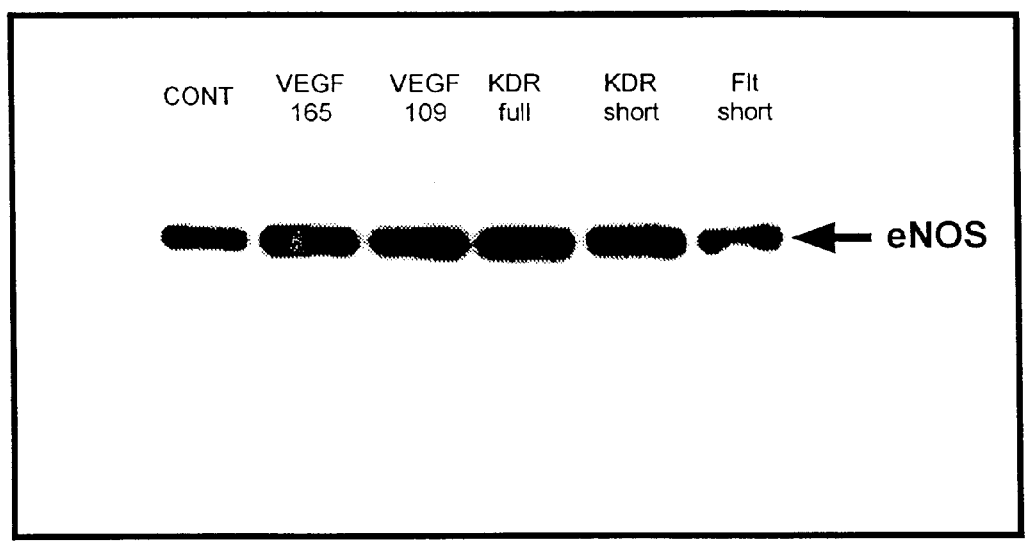
FIG. 10 is a Western blot showing the eNOS expression levels in endothelial cells treated by VEGF$_{165}$, VEGF$_{110}$, two KDR selective VEGF variants (KDR-full and KDR-short), or a Flt selective variant (Flt-short).

The VEGF variants identified and characterized in Examples 6–11 were used to illustrate the specific correlation of KDR receptor activity with eNOS upregulation. Methods and materials used in this study were as described above in Example 1. ACE cells were treated with 500 pM specific VEGF variants for 2 days. eNOS protein was detected by Western blot. FIG. 10 shows that both $VEGF_{65}$ and $VEGF_{110}$, a heparin binding domain-deficient mutant with normal binding to KDR and FLT-1, induced a similar degree of eNOS expression. The VEGF variants LK-VRB-2f (KDR-full) and LK-VRB-2s* (KDR-short) showed highly specific binding to the KDR receptor (Table 6). A FLT-specific variant (Flt-short) was used for comparison. As the shown in FIG. 10, Both KDR-specific variants markedly up-regulated eNOS expression, whereas the FLT-1 selective binding variant (FLT-sel) failed to do so. These data suggest that the identified KDR specific VEGF variants can replace wild type VEGF for use in up-regulating eNOS and treating disorders or conditions associated with abnormal eNOS activities or deficiencies in NO release or production.

Example 13

In Vivo Down-Regulation of eNOS by VEGF Antagonists

Modulation of endogenous eNOS by VEGF activity was tested in vivo in a mouse model. A chimeric protein, muFlt-IgG, containing a mutant Flt receptor, was used as a VEGF antagonist in this study. Mice were treated with muFlt-IgG or a control antibody (anti-gp120) at 25 mg/day, I.P. for 14 days. At the end of study, the livers were harvested and homogenized. Then, tissue homogenate was immunoprecipitated with an anti-eNOS monoclonal antibody. The eNOS content was detected by Western blot as described in Example 1.

Figure 11:
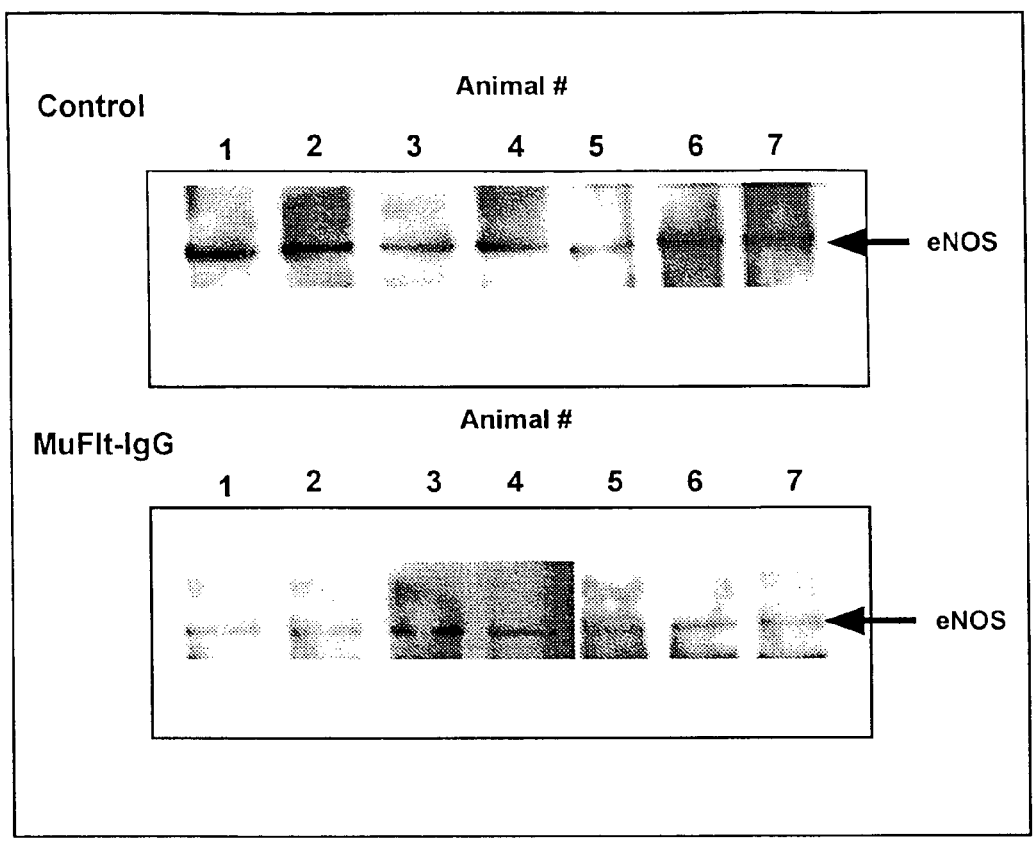
FIG. 11 is a Western blot data showing the in vivo eNOS expression affected by a VEGF antagonist (MuFlt-IgG).

FIG. 11 shows that the eNOS expression level in mice treated with MuFlt-IgG is significantly reduced. Thus, the results suggest that VEGF antagonist down-regulates eNOS expression in vivo, and implies a role for endogenous VEGF in the regulation of eNOS.

Example 14

Modulation of eNOS Activity by VEGF

Figure 12:
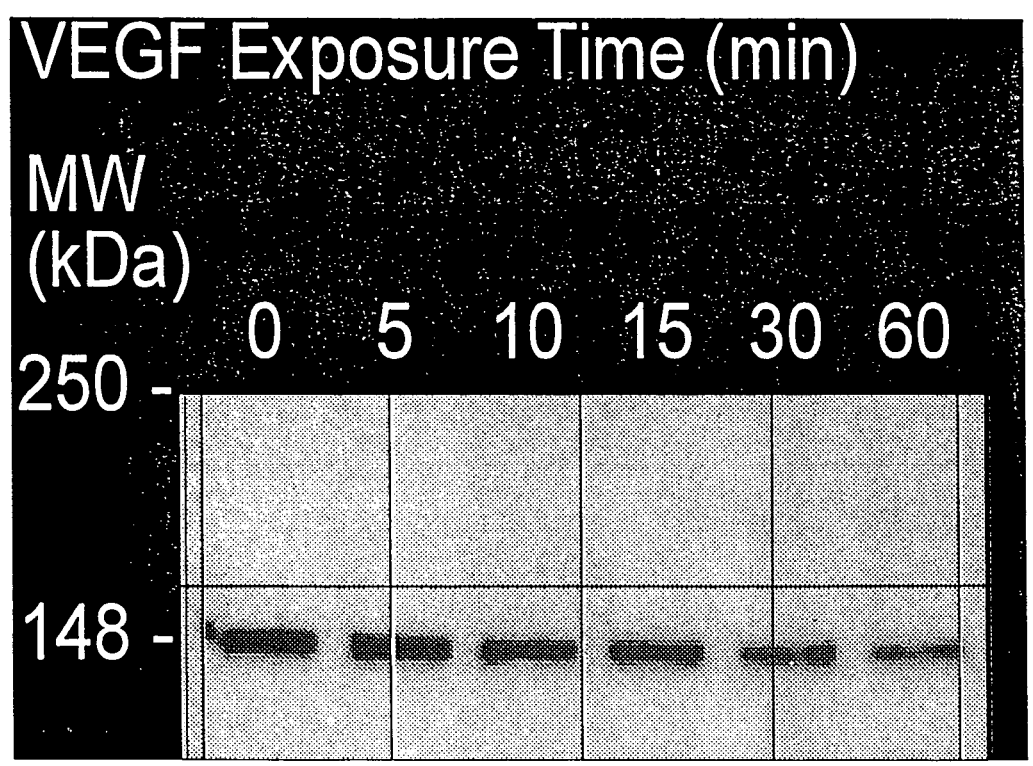
FIG. 12 is a Western blot showing the phosphotyrosine levels of eNOS in endothelial cells treated with VEGF for different time courses.

To further elucidate the role of VEGF in modulating the eNOS activity and endogenous NO release, the phosphotyrosine levels of eNOS post-VEGF stimulation were examined. In this time-course study, endothelial cells were first treated with VEGF for 0, 5, 10 15 30 or 60 minutes. Cells were lysed in a buffer containing tyrosine phosphatase inhibitors (sodium vanadate and sodium fluoride). Cell lysates were first immunopreciptated with an anti-eNOS antibody, and then immunoblotted with an anti-phosphotyrosine antibody. Phosphotyrosine levels were detected by Western blot as described in Example 1. FIG. 12 shows that as the VEGF treatment prolongs, the phosphotyrosine levels of eNOS are gradually reduced, which may in turn contribute to eNOS activation and sustained NO release.

Several eNOS associated proteins that attribute to eNOS activity were analyzed for their association/dissociation with eNOS under VEGF treatment. Endothelial cells were first treated with VEGF for 0 (control), 1, 5, 15, 30 or 60 minutes. Cell lysates were immunoprecipitated with an anti-eNOS antibody, and then immunoblotted with an antibody against α-caveolin, PLC-γ, Hsp90 or Hsp70 for Western blot analysis. The results show that VEGF significantly reduces eNOS association levels of caveolin and PLC-γ, even at short exposure time (1 minute). Meanwhile, VEGF can increase the levels of Hsp90 and Hsp70 associated with eNOS. The results suggested that VEGF can regulate eNOS activity by modulating its association with various proteins.

The foregoing written description is considered to be sufficient to enable one skilled in the art to practice the invention. Various modifications of the invention in addition to those shown and described herein will become apparent to those skilled in the art from the foregoing description and fall within the scope of the appended claims.

We claim:

1. A method of treating a nitric oxide (NO) associated disorder in a mammal, wherein the disorder is hypertension, thrombosis, angins, atherosclerosis, or heart failure, comprising administering to said mammal an effective amount of VEGF receptor agonist that exhibits selective binding affinity for a KDR receptor and induces NO production in the mammal, wherein the agonist comprises a VEGF variant having:
   a) one or more amino acid substitutions at or between residues F17 to Y15, wherein one or more of M18, Y21, O22, or Y25 is substituted; and
   b) one or more amino acid substitutions at or between residues D63 to E67;
   wherein the binding affinity of the agonist for FLT-1 receptor is reduced as compared to the binding affinity of native VEGF for FLT-1 receptor.

2. The method of claim 1 wherein said mammal is a human.

3. The method of claim 1 wherein said effective amount of VEGF receptor agonist enhances nitric oxide production in said mammal.

4. The method of claim 1, wherein the amino acid substitution(s) of (b) comprises D63S, G65M, or L66R.

5. The method of claim 4, wherein the amino acid substitutions of (b) comprise D63S, G65M, and L66R.

6. The method of claim 1, wherein the amino acid substitution(s) of (a) comprises one or more of M18E, Y21L, Q22R, or Y25S.

7. The method of claim 6, wherein the amino acid substitutions of (a) comprise M18E, Y21L, Q22R, and Y25S.

8. The method of claim 1, wherein the VEGF variant comprises one of the following combinations of amino acid substitutions:
   (a) M18E, D63S, G65M, and L66R;
   (b) Y21L, D63S, G65M, and L66R;
   (c) Q22R, D63S, G65M, and L66R;
   (d) Y25S, D63S, G65M, and L66R;
   (e) M18E, Y21L, D63S, G65M, and L66R;
   (f) M18E, Q22R, D63S, G65M, and L66R;
   (g) M18E, Y25S, D63S, G65M, and L66R;
   (h) Y21L, Q22R, D63S, G65M, and L66R;
   (i) Y21L, Y25S, D63S, G65M, and L66R;
   (j) Q22R, Y25S, D63S, G65M, and L66R;
   (k) M18E, Y21L, Q22R, D63S, G65M, and L66R;
   (l) M18E, Q22R, Y25S, D63S, G65M, and L66R;
   (m) Y21L, Q22R, Y25S, D63S, G65M, and L66R;
   (n) M18E, Y21L, Q22R, Y25S, and D63S;
   (o) M18E, Y21L, Q22R, Y25S, and G65M:
   (p) M18E, Y21L, Q22R, Y25S, and L66R;
   (q) M18E, Y21L, Q25R, Y25S, D63S, and G65M;
   (r) M18E, Y21L, Q22R, Y25S, D63S, and L66R;
   (s) M18E, Y21L, Q22R, Y25S, G65M, and L66R; or
   (t) M18E, Y21L, Q22R, Y25S, D63S, G65M, and L66R.

9. The method of claim 1, wherein NO production is sustained for more than 24 hours.

10. The method of claim 1, wherein NO production is sustained for at least 2 days.

11. The method of claim 1, wherein NO production is sustained for at least 3 days.

12. The method of claim 1, wherein NO production is sustained for at least 4 days.

* * * * *

UNITED STATES PATENT AND TRADEMARK OFFICE
CERTIFICATE OF CORRECTION

| | | |
|---|---|---|
| PATENT NO. | : 7,078,382 B1 | Page 1 of 1 |
| APPLICATION NO. | : 09/700806 | |
| DATED | : July 18, 2006 | |
| INVENTOR(S) | : Shen et al. | |

It is certified that error appears in the above-identified patent and that said Letters Patent is hereby corrected as shown below:

Column 27
Line 64 "add water to] liter" should read --add water to 1 liter--

Column 39
Line 55 "angins" should read --angina--
Line 63 "O22" should read --Q22--

Signed and Sealed this

Ninth Day of January, 2007

JON W. DUDAS
*Director of the United States Patent and Trademark Office*